(12) United States Patent
Scoones

(10) Patent No.: US 12,564,563 B2
(45) Date of Patent: Mar. 3, 2026

(54) COMPOSITION AND METHODS FOR TREATING PATHOGENIC INFECTIONS ON WOUNDS

(71) Applicant: JVS Products Ltd., Wiltshire (GB)

(72) Inventor: Robert Scoones, Wiltshire (GB)

(73) Assignee: JVS Products Ltd., Wiltshire (GB)

( * ) Notice: Subject to any disclaimer, the term of this patent is extended or adjusted under 35 U.S.C. 154(b) by 814 days.

(21) Appl. No.: 17/788,210

(22) PCT Filed: Dec. 22, 2020

(86) PCT No.: PCT/GB2020/053342
§ 371 (c)(1),
(2) Date: Jun. 22, 2022

(87) PCT Pub. No.: WO2021/130483
PCT Pub. Date: Jul. 1, 2021

(65) Prior Publication Data
US 2023/0019880 A1      Jan. 19, 2023

(30) Foreign Application Priority Data
Dec. 23, 2019    (GB) ...................................... 1919234

(51) Int. Cl.
| | |
|---|---|
| *A61K 31/14* | (2006.01) |
| *A61K 31/047* | (2006.01) |
| *A61K 31/05* | (2006.01) |
| *A61K 31/785* | (2006.01) |
| *A61P 17/06* | (2006.01) |
| *A61P 31/04* | (2006.01) |
(Continued)

(52) U.S. Cl.
CPC ............ *A61K 31/14* (2013.01); *A61K 31/047* (2013.01); *A61K 31/05* (2013.01); *A61K*

*31/785* (2013.01); *A61P 17/06* (2018.01); *A61P 31/04* (2018.01); *A61P 31/10* (2018.01); *A61P 31/12* (2018.01)

(58) Field of Classification Search
CPC ........ A01N 25/02; A01N 25/30; A01N 31/08; A01N 33/12; A01N 47/44; A61K 2800/591; A61K 2800/74; A61K 8/347; A61K 8/416; A61K 8/43; A61Q 17/005; Y02A 50/30
See application file for complete search history.

(56) References Cited

U.S. PATENT DOCUMENTS

| | | |
|---|---|---|
| 2009/0269380 A1 | 10/2009 | Baker, Jr. et al. |
| 2016/0212994 A1 | 7/2016 | Scoones |

FOREIGN PATENT DOCUMENTS

| | | |
|---|---|---|
| CN | 103751198 A | 4/2014 |
| CN | 104248776 A | 12/2014 |
| CN | 108324709 A | 7/2018 |
(Continued)

OTHER PUBLICATIONS

Office Action received in Japanese Application No. 2022-538405 dated Dec. 2, 2024, 5 pages.
(Continued)

*Primary Examiner* — Savitha M Rao
(74) *Attorney, Agent, or Firm* — Jeff B. Vockrodt; CM Law

(57) ABSTRACT

The invention relates to compositions for use in the treatment or prevention of pathogenic infections, rosacea, eczema and psoriasis in humans or animals. The compositions of the invention are also useful in the healing of wounds in a human or animal, and for killing or inactivating viruses on a surface.

6 Claims, 29 Drawing Sheets

Impetigo present

(51) Int. Cl.
A61P 31/10 (2006.01)
A61P 31/12 (2006.01)

(56) References Cited

FOREIGN PATENT DOCUMENTS

| | | | |
|---|---|---|---|
| CN | 109316536 | A | 2/2019 |
| GB | 2330773 | A | 5/1999 |
| JP | 2008512389 | A | 4/2008 |
| JP | 2011518844 | A | 6/2011 |
| WO | 2009010749 | A2 | 1/2009 |
| WO | 2016086280 | A1 | 6/2016 |

OTHER PUBLICATIONS

Communication pursuant to Article 94(3) received in European Application No. 20 838 262.2-1109 dated Feb. 4, 2025, 11 pages.
Search Report received in International Application No. PCT/GB2020/053342 dated Apr. 8, 2021, 4 pages.
Speight, et al., "Evaluation of the sporicidal activity of different chemical disinfectants used in hospitals against Clostridium difficile," ScienceDirect, Journal of Hospital Infection, vol. 79, Issue 1, Sep. 2011, 8 pages.
Written Opinion received in International Application No. PCT/GB2020/053342 dated Apr. 8, 2021, 11 pages.

FIG. 1(contd)

FIG. 1(contd)
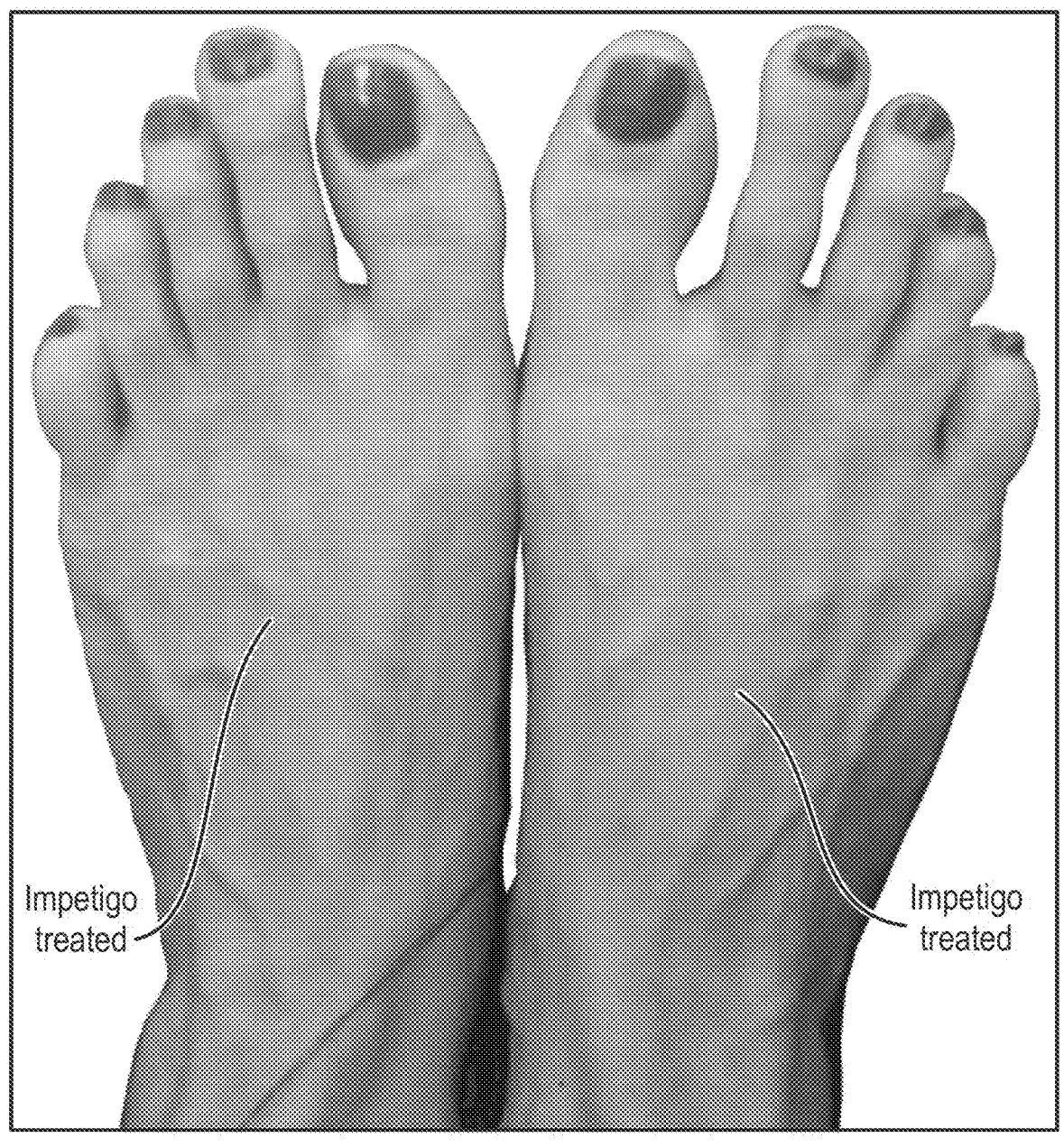

FIG. 2a

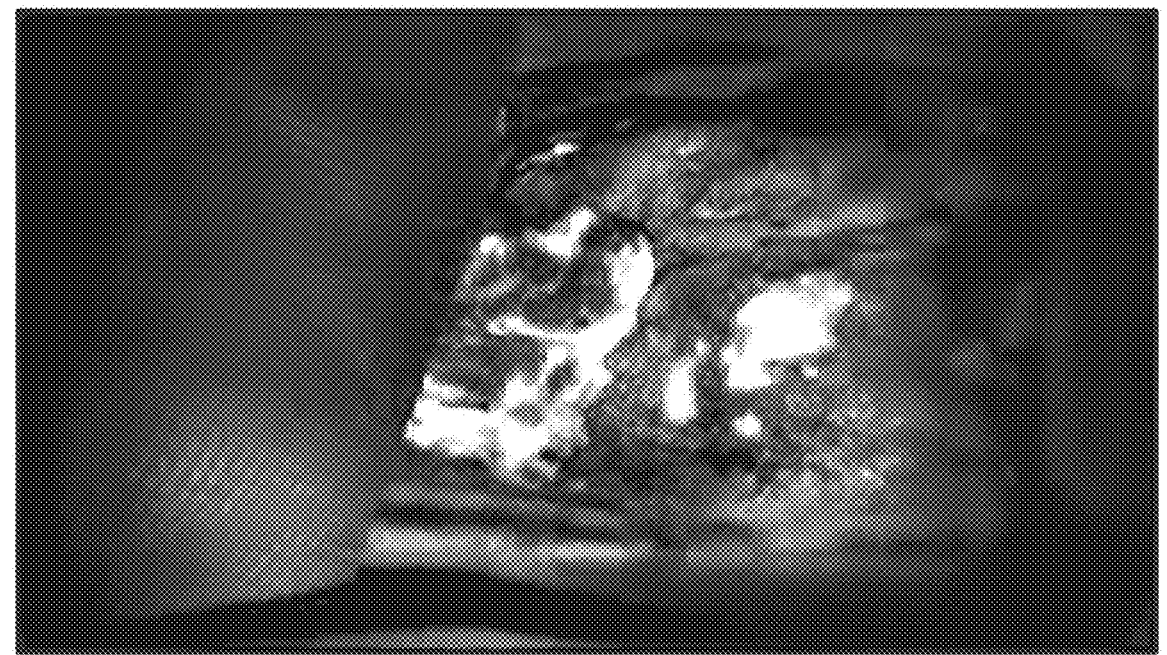
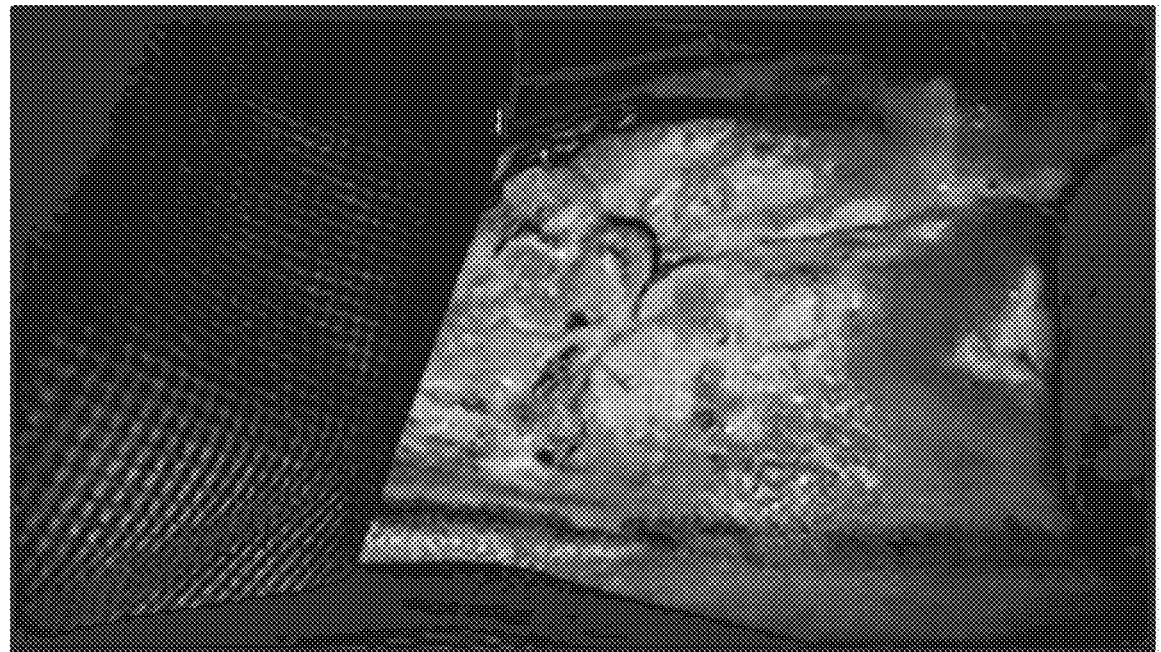
FIG. 2c
before treatment

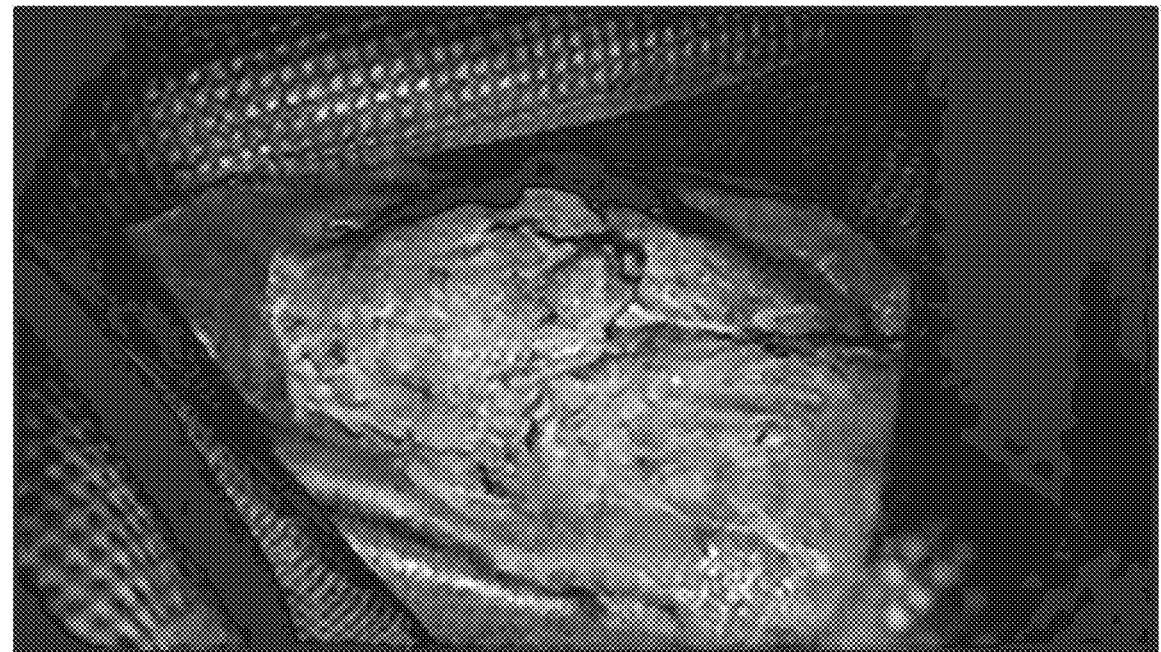
FIG. 2d
after treatment

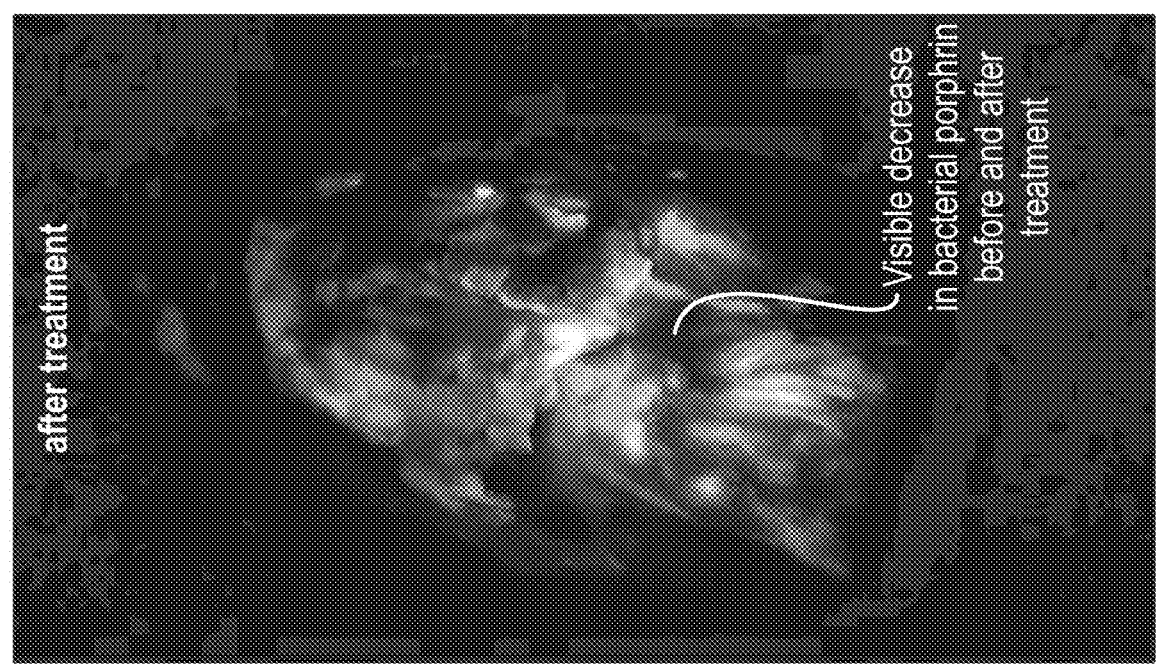
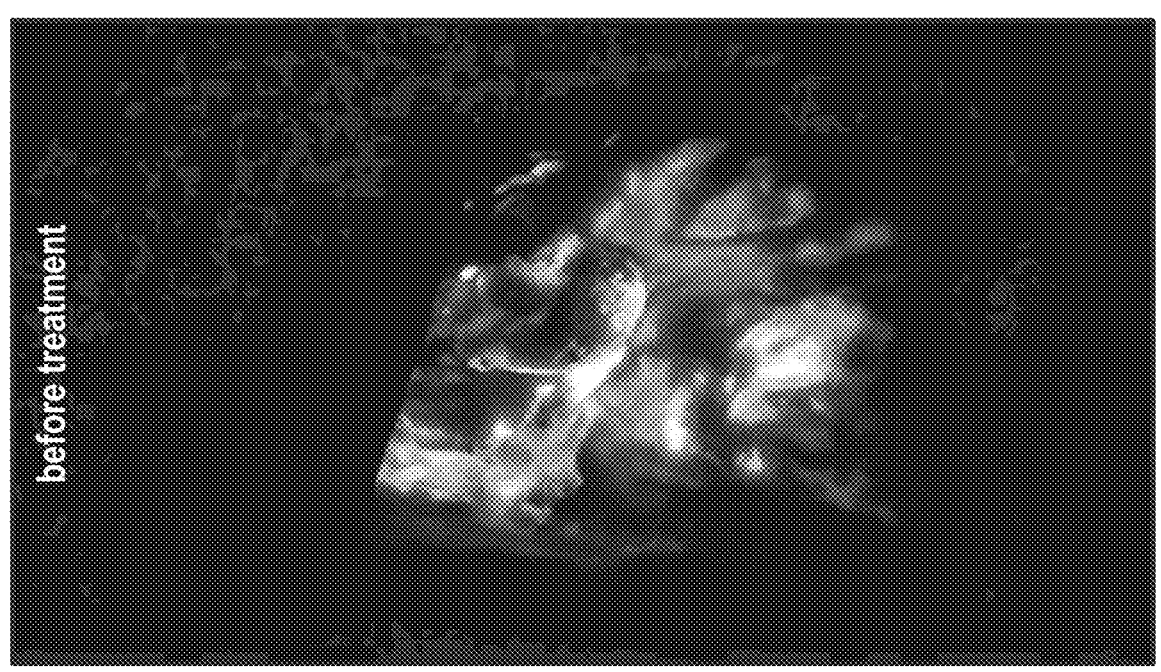
FIG. 2e

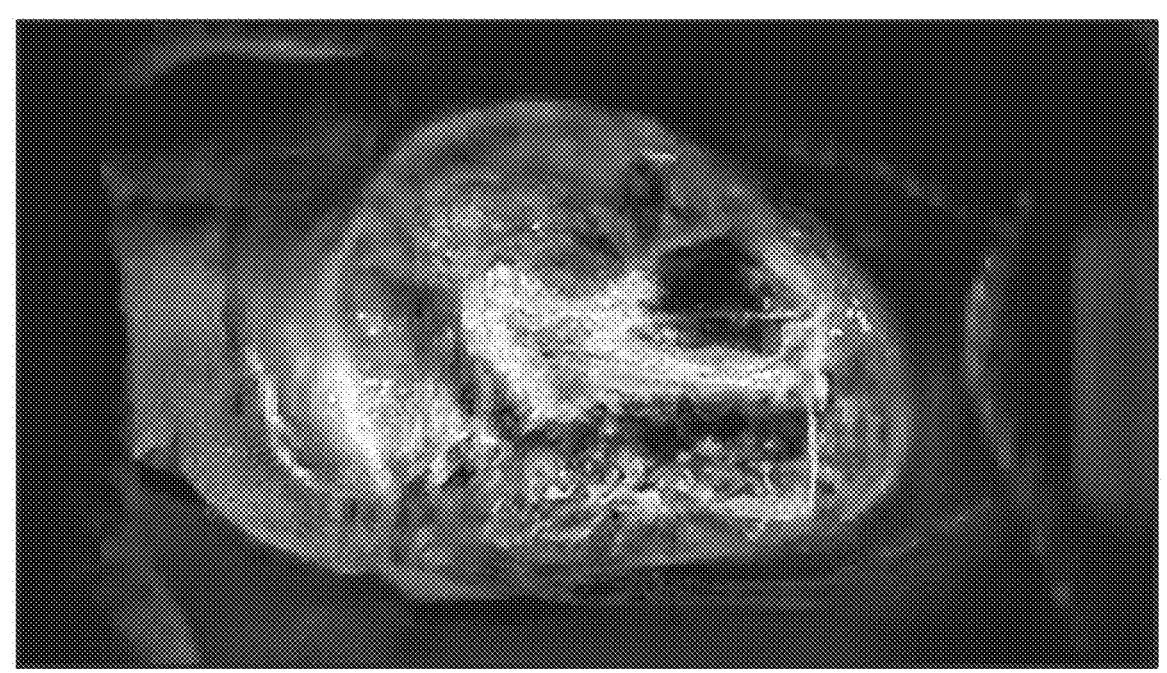
FIG. 2f
before treatment

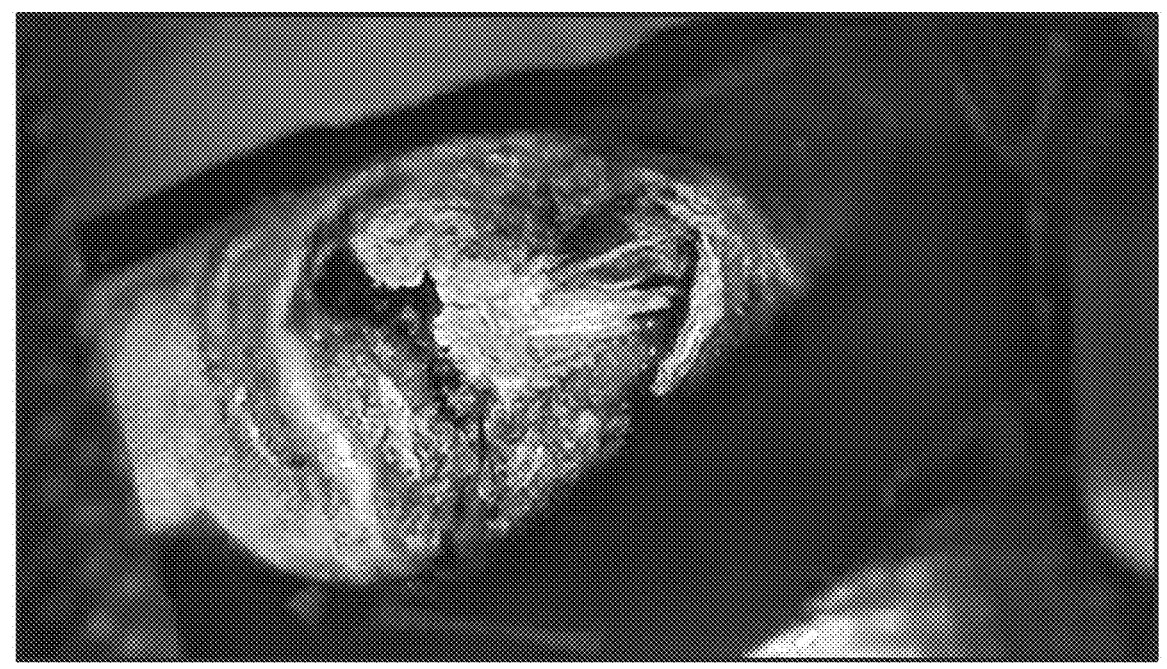
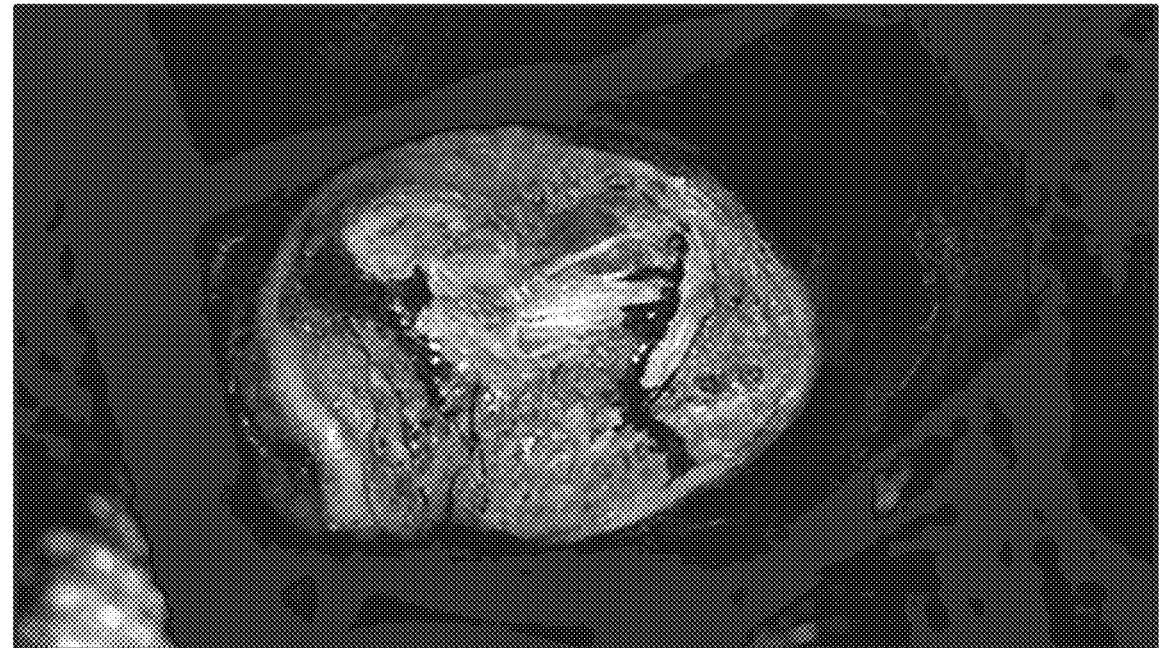
FIG. 2g
after treatment

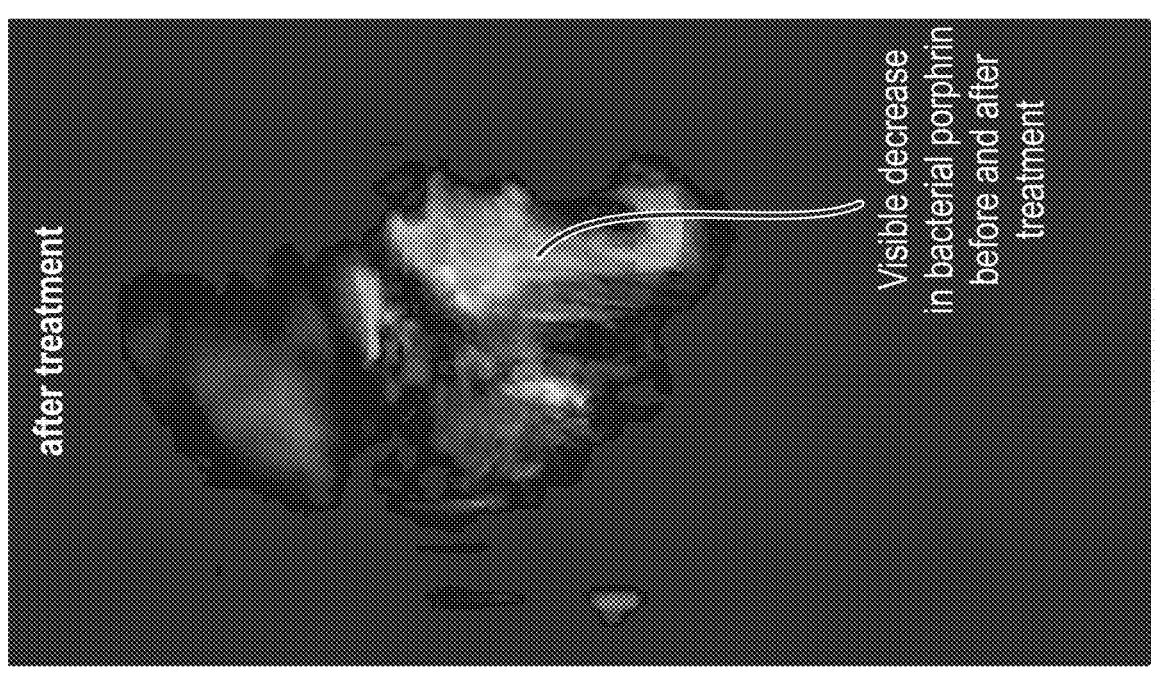
after treatment
Visible decrease
in bacterial porphrin
before and after
treatment
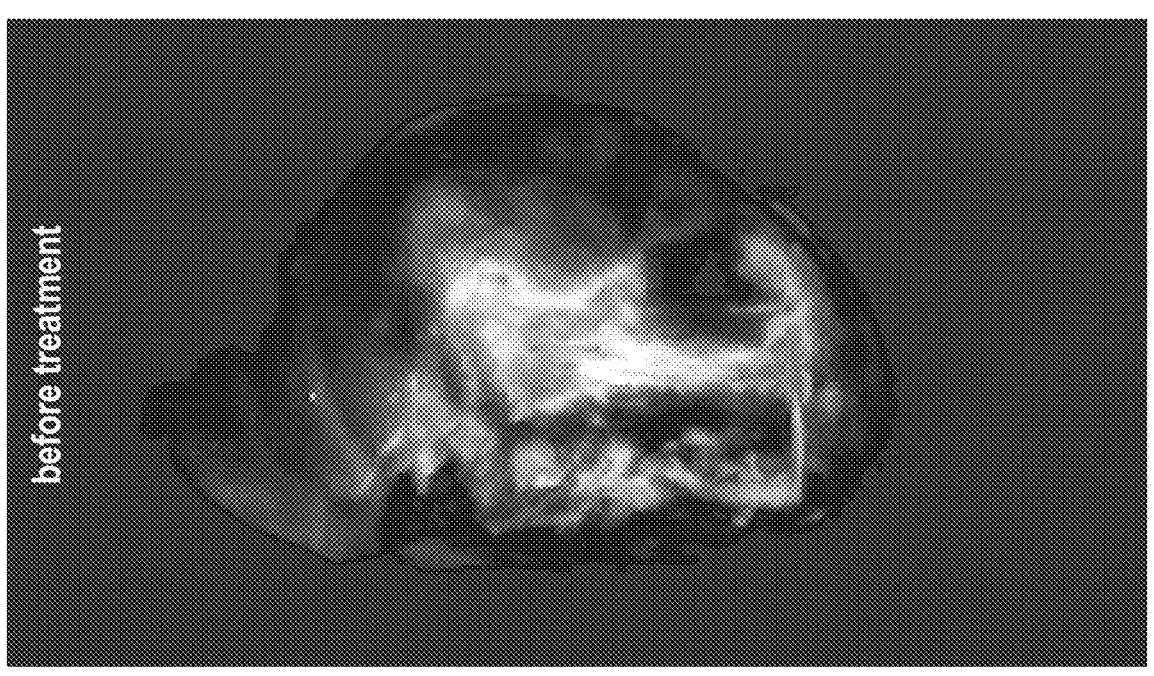
before treatment
FIG. 2h

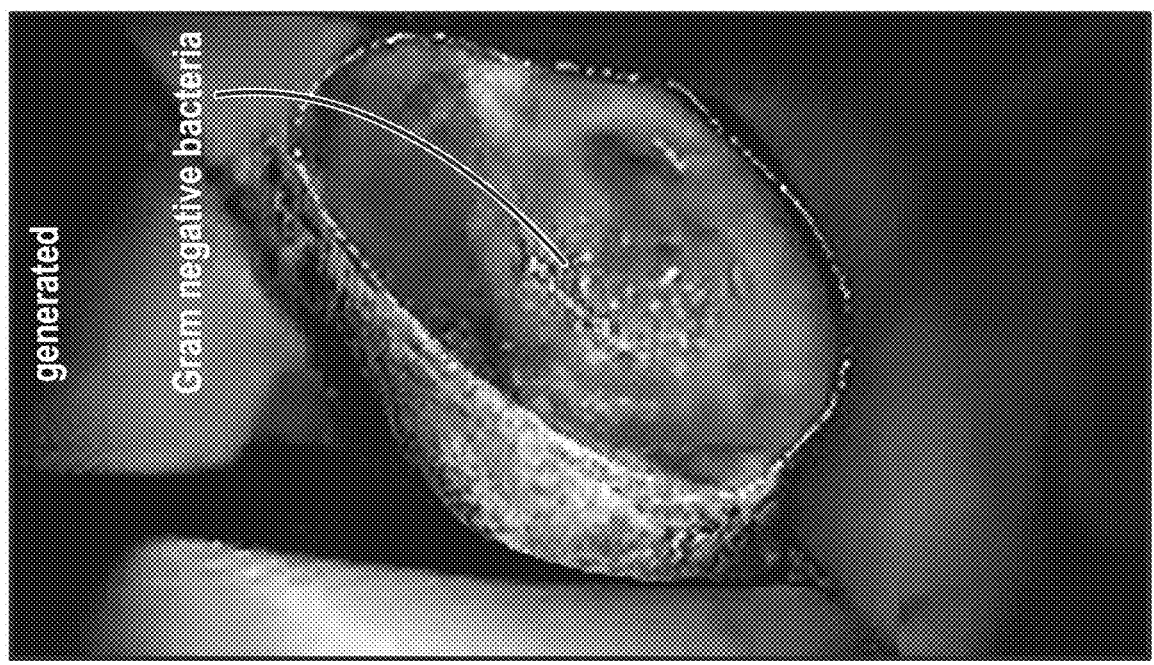
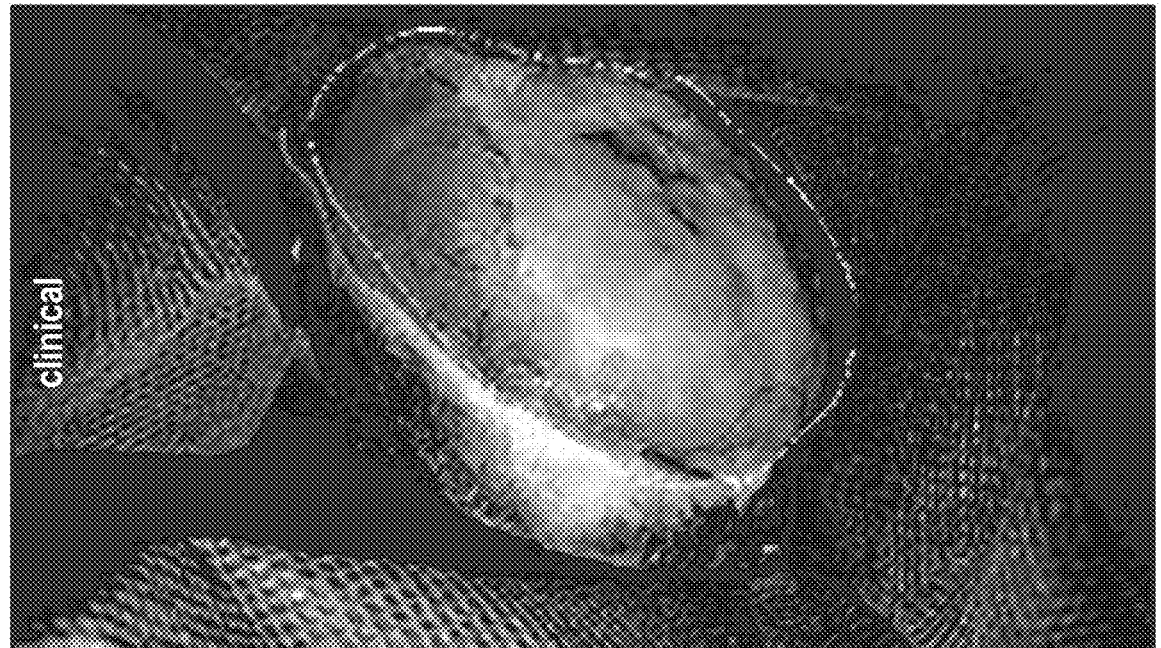
FIG. 2i
before treatment

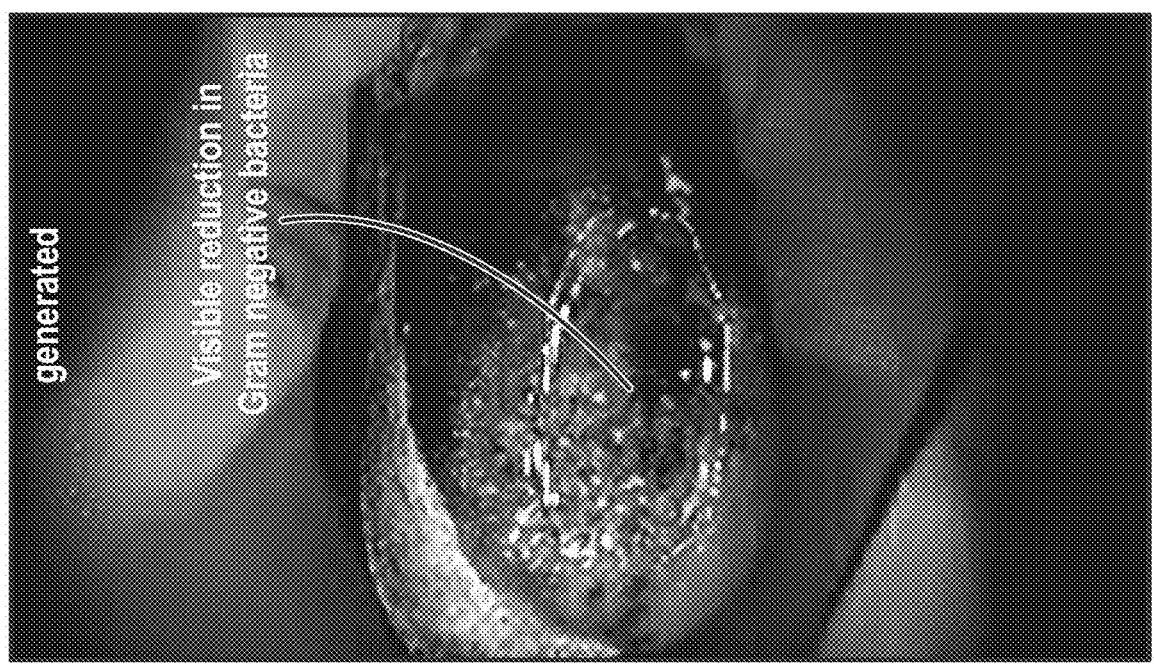
FIG. 2j
after treatment

FIG. 7a

| Contact time between virus and surface (minutes) | 48 hour Average pfu/cm² | 48 hour log-reduction | 24 hour Average pfu/cm² | 24 hour log-reduction | 1 hour Average pfu/cm² | 1 hour log-reduction Log10 reduction following 2 hours contact |
|---|---|---|---|---|---|---|
| 0 | 1116 | 0.35 | 1433 | 0.24 | 1650 | 0.18 |
| 0.5 (30s) | 580 | 0.63 | 276 | 0.957 | 385 | 0.81 |
| 5 | 1.6* | 2.92 | 0 | 3.39 | 0 | 3.39 |
| 10 | 0 | 3.39 | 0 | 3.39 | 0 | 3.39 |

*virus present in 1 out of 3 replicates

FIG. 7b

| Contact time between virus and surface (minutes) | Average pfu/cm² | log-reduction |
|---|---|---|
| 0 | 2100 | 0.075 |
| 0.5 (30s) | 222 | 1.05 |
| 5 | 0 | 3.39 |
| 10 | 0 | 3.39 |

3.39   Maximum log-reduction available for this assay, equivalent to no infectious virus remaining. HuCov-229E does not propagate to higher titres in this cell line.

FIG. 7c
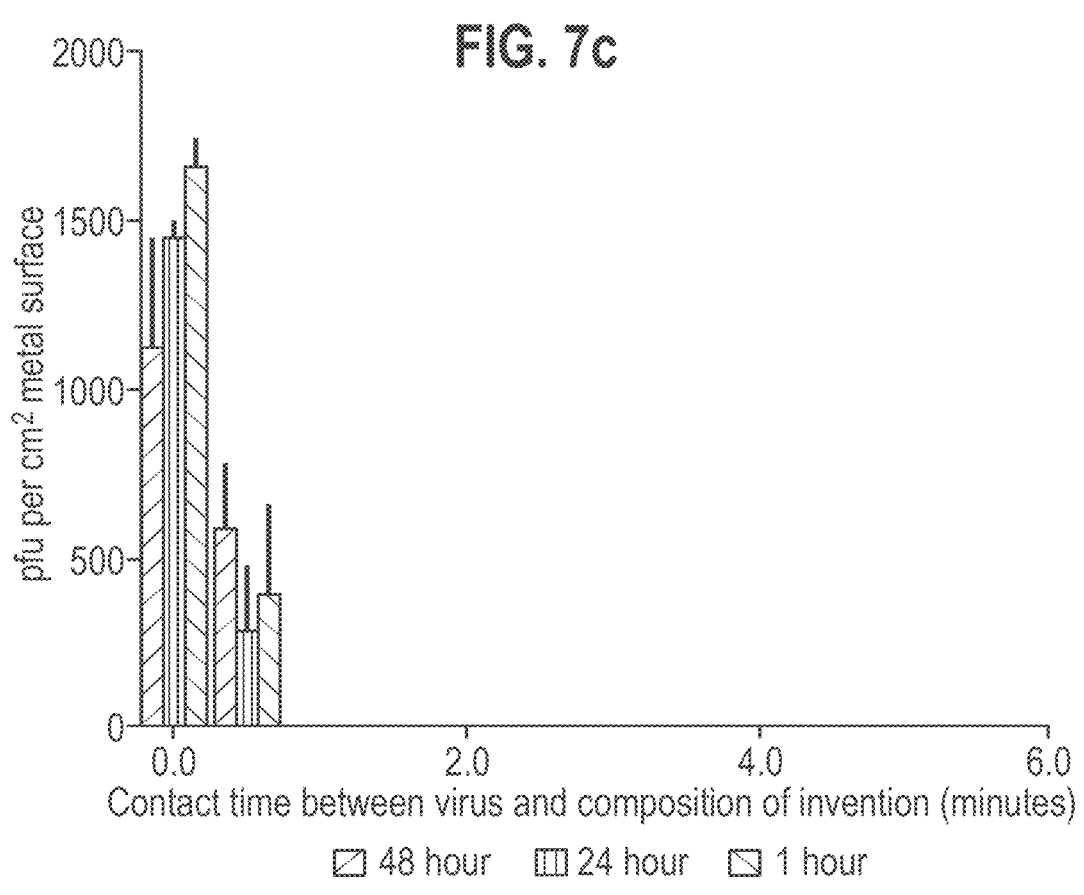
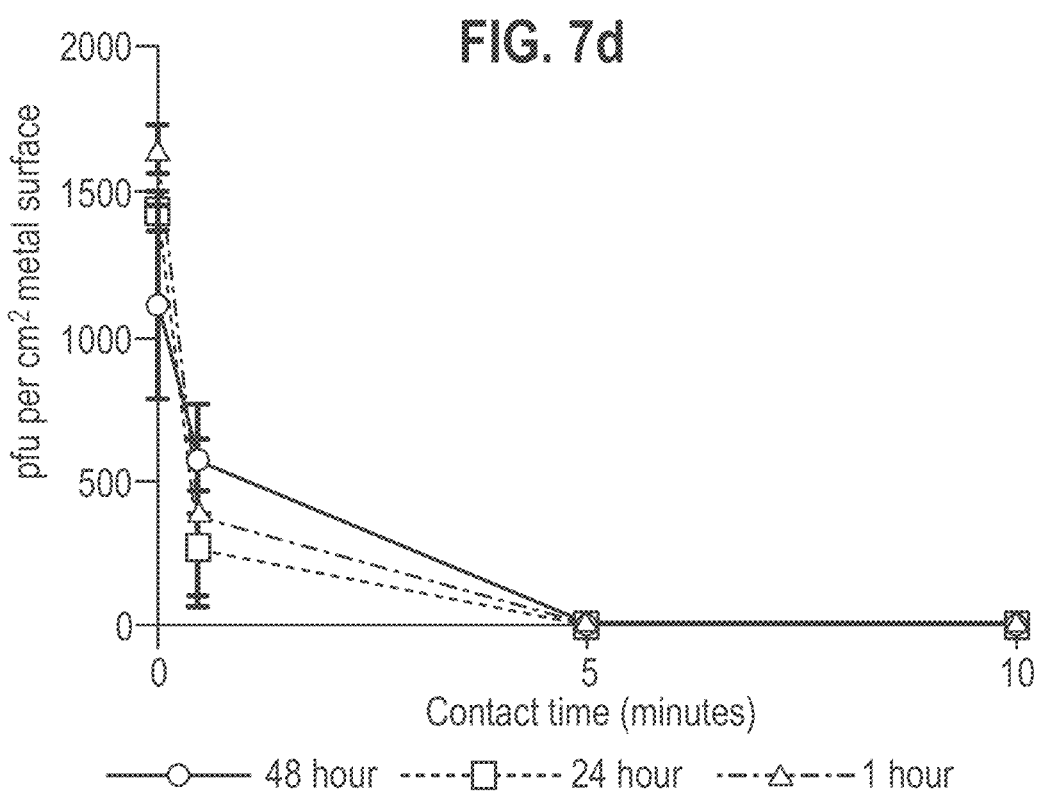
FIG. 7d

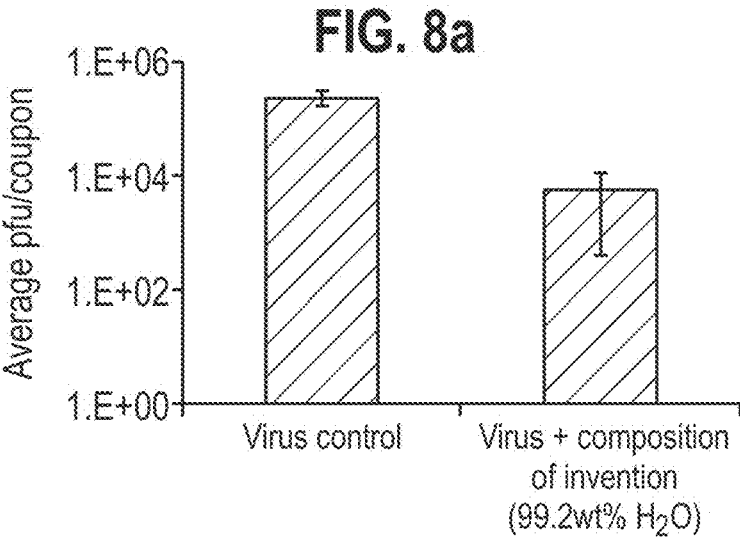
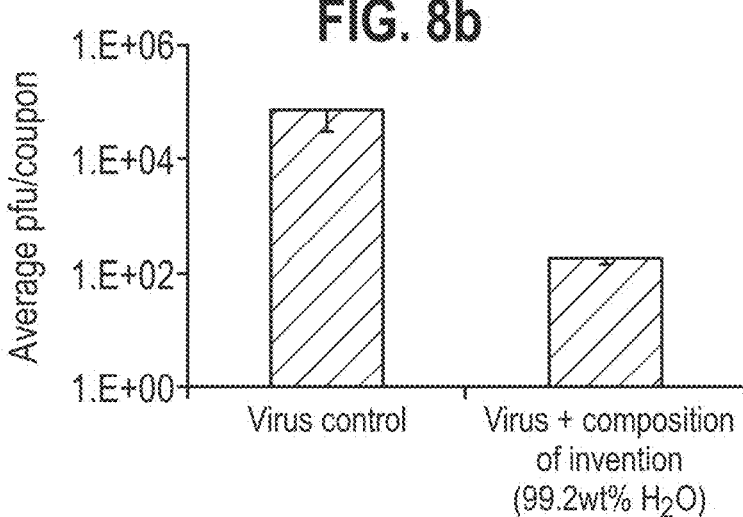
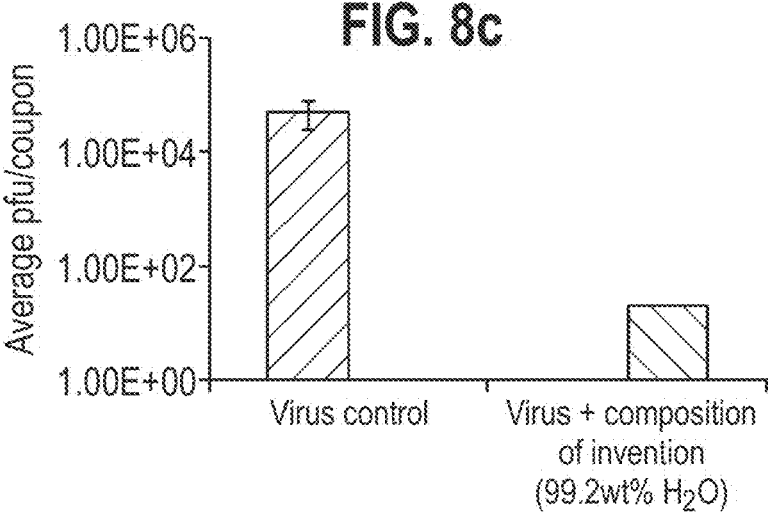

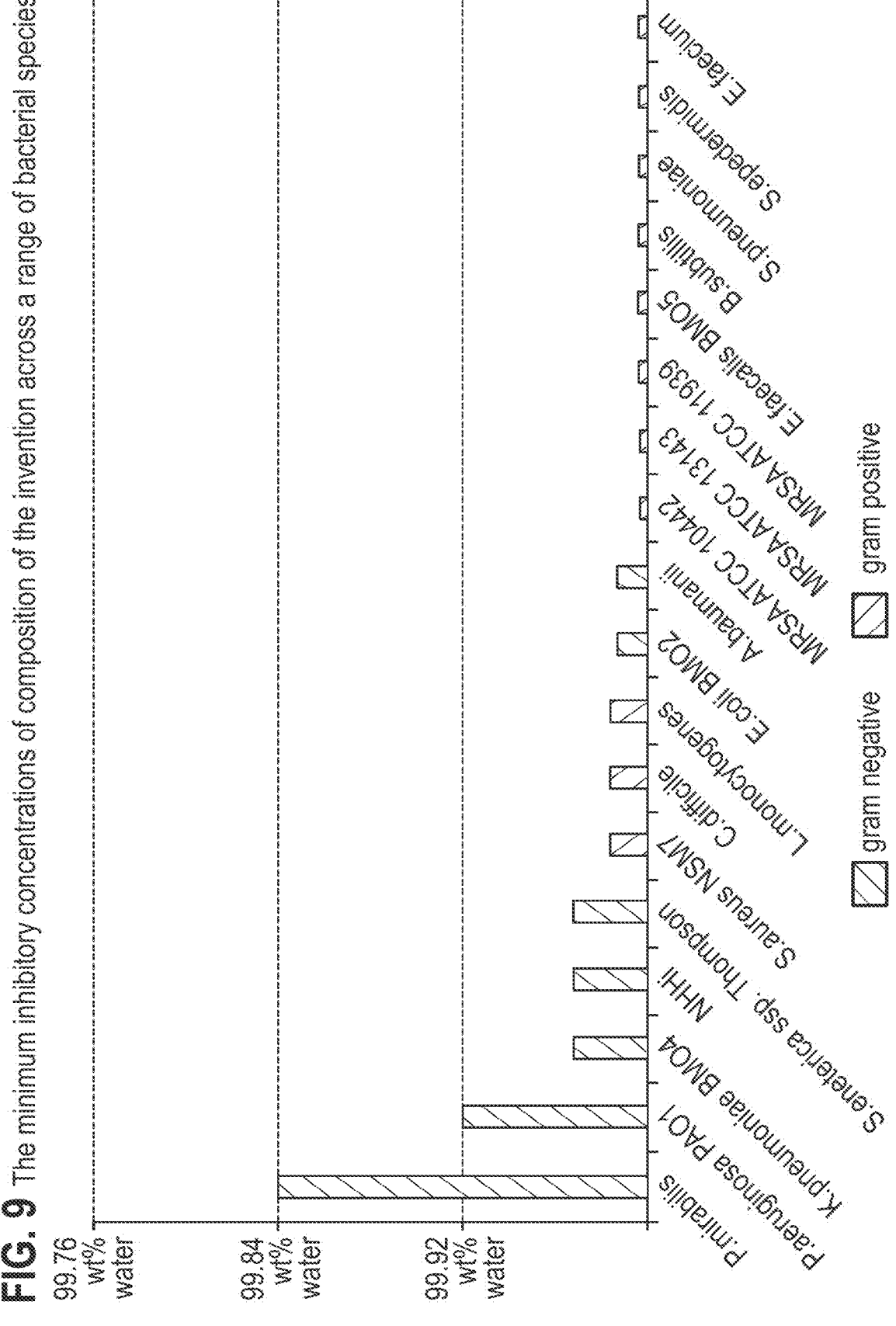
FIG. 9 The minimum inhibitory concentrations of composition of the invention across a range of bacterial species.

t=0, before treatment

FIG. 10a (contd)
t = 48h, after treatment with compositon of invention t=0

FIG. 10b (contd)
t=48h, no treatment

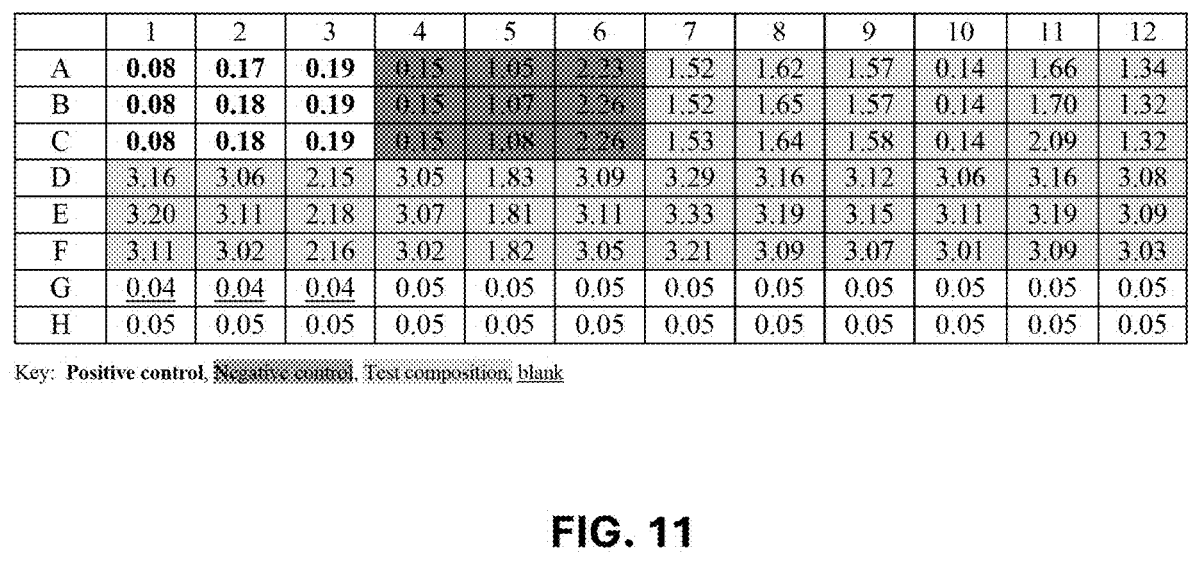

| | 1 | 2 | 3 | 4 | 5 | 6 | 7 | 8 | 9 | 10 | 11 | 12 |
|---|---|---|---|---|---|---|---|---|---|---|---|---|
| A | 0.08 | 0.17 | 0.19 | 0.15 | 1.05 | 2.33 | 1.52 | 1.62 | 1.57 | 0.14 | 1.66 | 1.34 |
| B | 0.08 | 0.18 | 0.19 | 0.15 | 1.07 | 2.26 | 1.52 | 1.65 | 1.57 | 0.14 | 1.70 | 1.32 |
| C | 0.08 | 0.18 | 0.19 | 0.15 | 1.08 | 2.26 | 1.53 | 1.64 | 1.58 | 0.14 | 2.09 | 1.32 |
| D | 3.16 | 3.06 | 2.15 | 3.05 | 1.83 | 3.09 | 3.29 | 3.16 | 3.12 | 3.06 | 3.16 | 3.08 |
| E | 3.20 | 3.11 | 2.18 | 3.07 | 1.81 | 3.11 | 3.33 | 3.19 | 3.15 | 3.11 | 3.19 | 3.09 |
| F | 3.11 | 3.02 | 2.16 | 3.02 | 1.82 | 3.05 | 3.21 | 3.09 | 3.07 | 3.01 | 3.09 | 3.03 |
| G | 0.04 | 0.04 | 0.04 | 0.05 | 0.05 | 0.05 | 0.05 | 0.05 | 0.05 | 0.05 | 0.05 | 0.05 |
| H | 0.05 | 0.05 | 0.05 | 0.05 | 0.05 | 0.05 | 0.05 | 0.05 | 0.05 | 0.05 | 0.05 | 0.05 |

Key: Positive control, Negative control, Test composition, blank

FIG. 11

COMPOSITION AND METHODS FOR TREATING PATHOGENIC INFECTIONS ON WOUNDS

TECHNICAL FIELD

The present invention relates to a composition for use in the treatment or prevention of pathogenic infections, such as bacterial, fungal and/or viral infections, in a human or animal. Specific examples of such infections include pathogenic infections in/on wounds, bacterial foot disease, impetigo and ringworm. The compositions of the invention may be used at very low concentrations and have been shown to be non-irritating to human or animal skin. The compositions of the invention are used as antiseptics.

The compositions of the invention are also useful in the treatment or prevention of rosacea, eczema and/or psoriasis in a human or animal.

Further, the compositions of the invention can be used to heal a wound in a human or animal, either on its own or whilst also treating or preventing a pathogenic infection in/on the wound.

In addition, the present invention relates to a method of killing or inactivating a virus on a surface by applying the composition of the invention to the surface. Examples of such viruses include norovirus and coronavirus.

BACKGROUND AND RELATED ART

Pathogenic infections, such as bacterial infections, can be serious infections which if left untreated develop into life-threatening conditions such as sepsis. Traditional treatments for pathogenic infections include antibiotics and antiseptics such as chlorohexidine. However, medical professionals are keen to avoid the use of antibiotics where possible to prevent the build-up of antibiotic resistance. Antiseptics are used to destroy or inhibit pathogenic microbes on living tissue without causing harmful effects to that tissue. However, many known antiseptics cause adverse effects such as allergic reactions, and many pathogenic infections have become resistant to treatments with known antiseptics. Thus, there is a need for new, antibiotic-free, agents for treating pathogenic infections.

Pathogenic infections in/on wounds are a particular problem because the pathogens can lead to local tissue damage and prevent the wound from healing (leading to chronic wounds such as venous leg ulcers). Thus, effective treatment of the pathogenic infection in/on the wound can be essential to the healing of the wound. The environment of a wound, particularly chronic wounds, is very different to that of hard surfaces and intact skin. Wounds contain a complex biological mix of damaged tissue, cells required for healing, protein-rich exudate and microbes. Thus, while disinfectants may be used to clean hard surfaces or intact skin, they are often inactivated in a wound environment. Thus, although an agent may prove to be an excellent disinfectant, this does not mean it will make a useful antiseptic for a wound. Indeed, many agents that can be used for the disinfection of unbroken skin prior to medical treatments (e.g. alcohol prior to venepuncture) can prove to be useless as wound antiseptics, i.e. they are not useful for treating pathogenic infections in/on wounds. The same is true even for some known antiseptics, i.e. some known antiseptics are inactivated in a wound environment.

Chronic wounds are even more difficult to treat owing to the fact that they usually contain biofilms-indeed, current estimates suggest that around 60% to 100% of chronic non-healing wounds contain a biofilm. The existence of biofilms in chronic wounds means the wounds often appear to be healing, only to become stagnant again. Biofilms are invisible, intricate structures composed of mixed strains of pathogens and are typically formed when certain types of microorganisms adhere themselves to the wound surface, and a viscous substance is then secreted. Pathogens within biofilms are much harder to eradicate with known treatments such as antibiotics and antiseptics than are planktonic cells. The complex architecture within biofilms produces stressful microenvironments leading to a spatio-physiologic heterogeneity of a population within the biofilm. This is likely the reason why viable-but-non-culturable (VBNC) and persister cells are often found in biofilms. Current recommendations for the management of chronic wounds include the removal of biofilm by physical debridement, or 'vigorous' cleaning, and accept that these actions will be ineffective in removing all the biofilm, therefore needing to be repeated.

Given that biofilm-related infections lead to significant morbidity and mortality, an effective treatment for pathogenic infections in/on wounds, particularly chronic wounds containing biofilms, is desirable. With this in mind, it is important that novel strategies to prevent and treat biofilms are developed.

Surfaces often come into contact with, provide an environment for, and provide a breeding ground for, potentially harmful viruses. It is common to clean surfaces with agents which act to mitigate and/or destroy potentially harmful viruses. The cleaning of surfaces in this way is beneficial to human and animal health because it prevents the spread of viruses and mitigates the chances of a subject or subjects contracting a viral infection by coming into contact with potentially harmful viruses. Surfaces of particular importance are those in a hospital and veterinary environment, e.g. a veterinary or hospital operating theatre. Thus, general cleaning is the cornerstone of infection control practice in healthcare settings. However, many of the agents currently used carry significant exposure hazards to human/animal health in the concentrations used, meaning clinical areas being decontaminated often have to be closed for several days. Also, the agents are often not fully effective against some of the common problematic viruses and lack any residual antimicrobial activity, making recontamination likely. Therefore, there is the need for effective, non-hazardous agents that could be employed in a range of settings to clean and decontaminate surfaces containing viruses.

Two specific viruses which are of particular importance are norovirus and coronavirus. Each year it is estimated that there are more than 267 million norovirus infections worldwide per year (including 23 million in the USA and up to 1 million in the U.K.). Norovirus outbreaks cost the National Health Service over £184 million (based on figures from 2002-2003) due to hospitalisations, and cost the USA an estimated $2 billion per year. While the infection is self-limiting, the symptoms are unpleasant, and patients shed high numbers of the virions for many days after getting ill. Human coronavirus 229E is a human respiratory pathogen that results in mild respiratory disease in healthy individuals but may cause serious disease in immunocompromised patients and individuals with multiple sclerosis. It is a Hazard Group 2 pathogenic virus used as a surrogate for coronaviruses responsible for more serious respiratory disease such as severe acute respiratory disease syndrome (SARS) and Middle East respiratory syndrome (MERS), which require higher containment facilities WO 2015/028806 describes a cleaning liquid and an aqueous mixture comprising the cleaning liquid for sanitising surfaces and water supplies. The cleaning liquid and aqueous mixtures in WO 2015/028806 are compositions according to this invention. The cleaning liquids and aqueous mixtures in WO 2015/028806 are also described as being useful in disinfection an area of skin. By disinfecting an area of skin it is meant that the cleaning liquids/aqueous mixtures kill or inhibit microbes on the surface of intact skin within a few minutes, e.g. to ensure a 'clean' area prior to the skin barrier being breached by, for example, a medical or surgical intervention. The World Health Organization defines a disinfectant as a chemical agent applied during cleaning to inanimate objects and materials to destroy or inhibit pathogenic microbes.

General Definitions

The term "comprising" encompasses "including" as well as "consisting", e.g. a composition "comprising" X may consist exclusively of X or may include something additional, e.g. X+Y. The term "comprising" used herein also encompasses "consisting essentially of", e.g. a composition "comprising" X may consist of X and any other components that do not materially affect the essential characteristics of the composition.

The term "about" in relation to a numerical value x is optional and means, for example, x+10%.

The term "animal" means a mammal or a bird.

A "pathogenic infection of skin", as described herein, is an infection of the skin caused by pathogens invading through the normal skin barrier due to a break in its integrity caused by injury (e.g. a wound) or a disease that impairs the skin barrier (e.g. impetigo). This invasion results in an inflammatory response, and if the pathogens have sufficient virulence it leads to widespread tissue infection and can result in, for example, sepsis. Treating such a pathogenic infection of skin is distinct from "disinfecting" an area of skin because disinfecting relates to killing or inhibiting microbes on the surface of intact skin in the short term (i.e. merely sterilizing the surface of intact skin), e.g. to ensure a 'clean' area prior to the skin barrier being breached by, for example, a medical or surgical intervention.

The term "skin" includes skin on/inside a mouth.

The term "wound" means an injury to living tissue (e.g. skin, muscle, etc.) caused by a cut, blow, or other impact, typically one in which the skin is cut or broken. Examples of wounds include burns, ulcers, cuts, grazes (abrasions) and punctures.

The term "heal" in relation to wounds means the accelerated closure/repair of the wound.

By "accelerated closure of the wound" it is meant that the wound is closed/repaired quicker (when the composition of the invention is used) than it would close/repair in the absence of the composition of the invention.

The term "chronic wound" means a wound which has failed to progress through the phases of healing in an orderly and timely fashion and has shown no significant progress toward healing in 30 days.

By "inactivating" a virus it is meant that the virus is put into a dormant state.

BRIEF DESCRIPTION OF THE FIGURES

The inventions will now be described, by way of example only, with reference to the accompanying figures.

FIGS. 2a-j: Multi-spectral before and after images showing treatment of Gram-positive and Gram-negative viablebut-non-culturable (VBNC) biofilm wounds and healing of the wounds with a composition of the invention.

FIGS. 7a-h: Killing and inactivating human coronavirus 229E using a composition of the invention.

FIG. 8a-c: Killing and inactivating murine norovirus using a composition of the invention.

FIG. 9: MICs for a range of Gram-positive and Gram-negative bacteria using a composition of the invention.

FIG. 11: The raw optical density of each well at 570 nm.

Figure 1:
FIG. 1: Before and after images of treatment of impetigo with a composition of the invention.

The figures are explained further in the "Examples" section.

DISCLOSURE OF THE INVENTION

This application has been drafted into sections to aid readability. However, this does not mean that each section is to be read in isolation. To the contrary, unless otherwise specified, each section is to be read with cross-referencing to the other sections, i.e. taking the entire application as a whole. No artificial separation of embodiments is intended, unless explicitly stated. Any of the compositions of the invention described herein may be used for any of the uses described herein.

Where a composition of the invention is said to comprise at least, for example, 99.2% water by weight, the other components in the composition are to be selected such that they do not exceed 0.8% by weight in total, i.e. so that the total amount in weight percent in the composition is 100%. Selection of component amounts in this technically sensible way is within the skilled person's skill set.

SUMMARY OF THE INVENTION

In a first aspect there is provided a composition of the invention, i.e. a composition comprising: a benzalkonium halide; a didecyl dimethyl ammonium halide; a poly hexamethylene biguanide salt; bronopol; and p-chloro-m-cresol, for use in the treatment or prevention of a pathogenic infection in a human or animal, preferably human. Thus, the compositions of the invention are used as antiseptics and are useful in the treatment or prevention of diseases/conditions associated with, i.e. caused by, a pathogenic infection. The pathogenic infection is preferably a pathogenic infection of skin, muscle tissue, connective tissue and/or skeletal tissue. Specific examples include pathogenic infections in/on a wound and impetigo.

Not only are the compositions of the invention able to treat or prevent various pathogenic infections, as shown in the examples, they are also useful in the treatment or prevention of Gram-positive and Gram-negative pathogenic infections containing biofilms, where the biofilms contain VBNC cells, such as chronic wounds (e.g. chronic burns). The compositions of the invention can also be used at low concentrations which are non-irritant to the skin.

In a second aspect there is provided a composition of the invention for use in the treatment or prevention of rosacea, psoriasis and/or eczema in a human or animal, preferably human. Thus, the composition of the invention can additionally treat or prevent other skin conditions, i.e. skin conditions which are not, or are not caused by, pathogenic infections.

In a third aspect there is provided a composition of the invention for use in healing a wound in a human or animal, preferably human, i.e. accelerating the time in which a wound closes. The composition of the invention may also heal wounds whilst treating or preventing a pathogenic infection in/on the wounds, i.e. whilst killing pathogens such as bacteria in/on the wounds.

In a fourth aspect there is provided a method of killing or inactivating a virus on a surface comprising applying the composition of the invention to the surface. Preferred viruses are norovirus and coronavirus. It has been found that the composition of the invention need only be used at low concentration to achieve this effect. Furthermore, the composition of the invention can be pre-coated on surfaces, i.e. the surface can be pre-treated, to prevent viral infections on the surface for up to 48 hours.

In a fifth aspect the invention relates to the composition of the invention for use as a medicament. In a sixth aspect the invention relates to the composition of the invention for use as an antiseptic, i.e. the composition of the invention is used as an antiseptic on the human or animal body, preferably the human body.

DETAILED DESCRIPTION OF THE INVENTION

The present invention relates to a composition of the invention comprising: a benzalkonium halide, a didecyl dimethyl ammonium halide, a poly hexamethylene biguanide salt, bronopol, and p-chloro-m-cresol, for use in the treatment or prevention of a pathogenic infection in a human or animal. Thus, the compositions of the invention are useful in the treatment or prevention of diseases/conditions associated with, i.e. caused by, a pathogenic infection.

The compositions of the invention are also useful treating or preventing rosacea, psoriasis and/or eczema, in healing wounds, i.e. accelerating the time in which a wound is closed, and in killing or inactivating viruses on surfaces.
Composition of the Invention The compositions of the invention may be any of the compositions disclosed on page 4, line 11 to page 7, line 2, page 8, line 7 to page 13, line 31, and claims 1-16 of WO 2015/028806 (which is hereby incorporated by reference), i.e. the composition of the invention may be any of the "cleaning liquids" or "aqueous mixtures" disclosed in WO 2015/028806. The compositions of the invention may also be any one of the compositions as defined herein.

The composition of the invention comprises: a benzalkonium halide, a didecyl dimethyl ammonium halide, a poly hexamethylene biguanide salt, bronopol, and p-chloro-m-cresol.

In an embodiment, the composition of the invention composition comprises: 0.04-0.2 wt % benzalkonium halide; 0.04-0.2 wt % decyl dimethyl ammonium halide; 0.04-0.2 wt % poly hexamethylene biguanide salt; 0.01-0.06 wt % bronopol; and 0.0005-0.005 wt % p-chloro-m-cresol.

In an embodiment, the benzalkonium halide is benzalkonium chloride, and/or the didecyl dimethyl ammonium halide is didecyl dimethyl ammonium chloride, and/or the poly hexamethylene biguanide salt is poly hexamethylene biguanide hydrochloride. In a preferred embodiment, the benzalkonium halide is benzalkonium chloride, the didecyl dimethyl ammonium halide is didecyl dimethyl ammonium chloride, and the poly hexamethylene biguanide salt is poly hexamethylene biguanide hydrochloride.

The composition may additionally comprise a solvent. Preferably, the solvent is ethanol. The solvent is preferably present in the composition in 0.05-0.3 wt %.

The composition may additionally comprise an alkylene glycol. Suitable alkylene glycols that may be used in the composition of the invention include ethylene glycol, propylene glycol, diethylene glycol, block copolymers of ethyleneoxide and propyleneoxide, any other alkylene glycol formed from combining alkylene oxides and/or any combination of alkylene glycols. In a preferred embodiment, the alkylene glycol is ethylene glycol. The alkylene glycol is preferably present in the composition in 0.01-0.07 wt %.

The alkylene glycol may be may be substituted, in whole or in part, with other alkylene glycols, for example: ethylene glycol, propylene glycol, diethylene glycol, block copolymers of ethyleneoxide and propyleneoxide (e.g. different types of Pluronic™ as sold by BASF™), any other alkylene glycol formed from combining alkylene oxides and/or any combination of alkylene glycols.

In a preferred embodiment, the composition additionally comprises ethanol and ethylene glycol, preferably 0.05-0.3 wt % of ethanol and 0.01-0.07 wt % of ethylene glycol.

Preferably, the composition of the invention does not include one or more siloxanes.

Preferably, the composition of the invention does not contain an antibiotic. Indeed, an advantage of the composition of the invention is that it is able to kill a wide range of pathogenic infections quickly and at low concentrations, without the need to use an antibiotic, which are often ineffective. Also, the build-up of antimicrobial resistance can be avoided by using the composition of the invention, instead of antibiotics.

In an embodiment the composition of the invention additionally comprises water. In an embodiment, the composition comprises at least 83.9% water by weight, or at least 96% water by weight, or at least 97% water by weight, or at least 98% water by weight, or at least 98.7% water by weight, or at least 99.0% water by weight, or at least 99.2% water by weight, or at least 99.5% water by weight, or at least 99.6% water by weight, or at least 99.7% water by weight, or at least 99.76% water by weight. Preferably, the composition comprises at least 99.2% water by weight or at least 99.76% water by weight.

As is shown in the examples, the inventors have found that the compositions of the invention are able to treat a variety of pathogenic infections and skin conditions such as psoriasis, heal wounds and kill or inactivate viruses even when used at surprisingly low concentrations, i.e. when the water content in the composition is high, for example at least 99.2% water by weight or even at least 99.76% water by weight.

Furthermore, as is described in Example 7, an additional advantage of the compositions of the invention is that they can be used effectively at very low concentrations such that the compositions are non-cytotoxic. For example, when the content of water in the composition is higher than about 99.5% by weight, e.g. higher than 99.76% by weight, the compositions of the invention are non-cytotoxic and yet surprisingly are still able to treat pathogenic infections in a human or animal, psoriasis, eczema and rosacea, and heal wounds, as described herein. The combination of non-cytotoxicity whilst maintaining efficacy in relation to the uses described herein was surprising.

Thus, in an embodiment, the composition of the invention comprises at least 99.76% water by weight and is for use in treating impetigo. In an embodiment, the composition of the invention comprises at least 99.76% water by weight and is for use in treating a fungal nail infection. In an embodiment, the composition of the invention comprises at least 99.76% water by weight and is for use in treating a bacterial infection in/on a wound. In an embodiment, the composition of the invention comprises at least 99.76% water by weight and is for use in healing a wound. In an embodiment, the composition of the invention comprises at least 99.76% water by weight and is for use in treating psoriasis.

In an embodiment, the composition of the invention comprises:

benzalkonium halide;

decyl dimethyl ammonium halide;

poly hexamethylene biguanide salt;

bronopol;

p-chloro-m-cresol;

solvent;

alkylene glycol; and water.

In another embodiment, the composition of the invention comprises:

0.04-0.2 wt % benzalkonium halide;

0.04-0.2 wt % decyl dimethyl ammonium halide;

0.04-0.2 wt % poly hexamethylene biguanide salt;

0.01-0.06 wt % bronopol;

0.0005-0.005 wt % p-chloro-m-cresol;

0.05-0.3 wt % solvent;

0.01-0.07 wt % alkylene glycol; and the balance being water.

In a preferred embodiment, the composition of the invention comprises:

benzalkonium chloride;

decyl dimethyl ammonium chloride;

poly hexamethylene biguanide hydrochloride;

bronopol;

p-chloro-m-cresol;

ethanol;

ethylene glycol; and water.

In a particularly preferred embodiment, the composition of the invention comprises:

0.04-0.2 wt % benzalkonium chloride;

0.04-0.2 wt % decyl dimethyl ammonium chloride;

0.04-0.2 wt % poly hexamethylene biguanide hydrochloride;

0.01-0.06 wt % bronopol;

0.0005-0.005 wt % p-chloro-m-cresol;

0.05-0.3 wt % ethanol;

0.01-0.07 wt % ethylene glycol; and the balance being water.

In a more preferred embodiment, the composition of the invention comprises:

0.15 wt % benzalkonium chloride;

0.15 wt % decyl dimethyl ammonium chloride;

0.165 wt % poly hexamethylene biguanide hydrochloride;

0.045 wt % bronopol;

0.002 wt % p-chloro-m-cresol;

0.245 wt % ethanol;

0.05 wt % ethylene glycol; and 99.2 wt % water.

In another more preferred embodiment, the composition of the invention comprises:

0.045 wt % benzalkonium chloride;

0.045 wt % decyl dimethyl ammonium chloride;

0.0495 wt % poly hexamethylene biguanide hydrochloride;

0.0135 wt % bronopol;

0.0006 wt % p-chloro-m-cresol;

0.0735 wt % ethanol;

0.015 wt % ethylene glycol; and 99.76 wt % water.

The composition of the invention may be formulated in any way that is suitable for application to a human or animal. Preferred examples are liquids, foams, moisturisers and gels.

The compositions of the invention may be applied to the human or animal by any suitable means, e.g. by wipe, spray, sponge, cloth, towel, mouthwash or dressings impregnated with the composition. Preferably, the composition is applied to the human or animal by wipe or spray or dressings impregnated with the composition. In another preferred embodiment, the composition of the invention is applied to human or animal skin in/on the mouth by a mouthwash, i.e. the composition of the invention is used as a mouthwash.

Uses of the Compositions of the Invention (i) Treating or Preventing a Pathogenic Infection The composition of the invention is useful in the treatment or prevention of a pathogenic infection in a human or animal, preferably human. Most preferably, the compositions of the invention as defined herein are useful in the treatment of a pathogenic infection in a human or animal, preferably human. Thus, the compositions of the invention are useful in the treatment or prevention of diseases/conditions associated with, i.e. caused by, a pathogenic infection.

The compositions are also useful in preventing the transmission of a pathogenic infection from a human or animal to another human or animal, preferably human to human.

Pathogenic infections that can be treated or prevented by the composition of the invention include bacterial infections, fungal infections and viral infections.

Examples of bacterial infections that may be treated or prevented by the composition of the invention include bacterial infections in/on wounds, impetigo, ulcers (including diabetic foot ulcers and bed/pressure sores), boils, leprosy, bacterial foot disease, cellulitis, abscesses, interdigital dermatitis and erysipelas. Particularly preferred bacterial infections are bacterial infections in/on wounds (i.e. the wound comprises at least one bacteria), and impetigo. By treatment of a bacterial infection in/on a wound, it is meant that the bacteria in/on the wound are killed, i.e. removed, in whole or in part, by the composition of the invention.

Other particularly preferred bacterial infections that are treated or prevented by the compositions of the invention are bacterial infections comprising, i.e. caused at least in part by, *S. aureus* (e.g. MRSA), *P. aeruginosa*, *E. coli*, *E. hirae*, *A. baumannii*, *Corynebacterium amycolatum*, *Corynebacterium striatum*, and/or *Klebsiella* sp., preferably *S. aureus*, *P. aeruginosa* and/or *Klebsiella* sp.

In a preferred embodiment, the bacterial infection comprises rod-shaped (e.g. *klebsiella* sp.) and/or spherical-shaped (e.g. *S. aureus*) bacteria. More preferably, the bacterial infection comprises rod-shaped bacteria.

Examples of fungal infections that may be treated or prevented by the composition of the invention include fungal infections in/on wounds, fungal nail infection, fungal foot infections, ulcers, yeast infection, athlete's foot, and ringworm. Particularly preferred fungal infections are fungal infections in/on wounds (i.e. the wound comprises at least one fungus) and fungal nail infections. By treatment of a fungal wound, it is meant that the fungi in/on the wound are killed, i.e. removed, (in whole or in part), by the composition of the invention.

Examples of viral infections that may be treated or prevented by the composition of the invention include norovirus, coronavirus, herpes, cold sore virus, HPV, chicken pox, shingles, measles, warts, molluscum contagiosum. Particularly preferred viruses are norovirus and coronavirus.

In an embodiment, the composition of the invention is used in the treatment or prevention of a bacterial infection and/or fungal infection. In a preferred embodiment, the pathogenic infection is a bacterial infection. In another preferred embodiment, the pathogenic infection is a fungal infection.

In an embodiment the pathogenic infection is a pathogenic infection of human or animal skin, muscle tissue, connective tissue and/or skeletal tissue. In a preferred embodiment the pathogenic infection is a pathogenic infection of human or animal skin.

In preferred embodiment, the composition of the invention is applied topically to the human or animal. Where the pathogenic infection is a pathogenic infection of skin, the composition may be applied to the skin of the human or animal directly. Thus, in a preferred embodiment the composition of the invention is applied topically to human or animal skin.

In a preferred embodiment, the pathogenic infection is in/on a wound and thus the composition of the invention is for treating or preventing a pathogenic infection in/on a wound, i.e. killing a pathogenic infection in/on a wound. In a preferred embodiment, the wound is a bacterial and/or fungal wound. In a more preferred embodiment, the wound is a bacterial wound, i.e. the wound contains bacteria that are killed, i.e. removed, in whole or in part, by the composition of the invention. Preferably, the bacteria in/on the wound comprises one or more of *S. aureus, P. aeruginosa, E. coli, E. hirae, A. baumannii, Corynebacterium amycolatum, Corynebacterium striatum*, and/or *klebsiella* sp., more preferably one or more of *S. aureus, P. aeruginosa* and/or *klebsiella* sp. The examples show that the composition of the invention has bactericidal activity against these common wound bacteria when tested under "dirty conditions" and in real-life wounds. In another preferred embodiment, the bacterial infection in/on the wound comprises rod-shaped and/or spherical-shaped bacteria, more preferably rod-shaped bacteria. In some embodiments the wound is a cut, burn, puncture or ulcer.

The wound may be a chronic wound. As is shown in the examples, the composition of the invention is capable of treating chronic wounds because its spectrum of activity encompasses Gram-positive and Gram-negative bacteria and it has rapid bactericidal and fungicidal actions, with excellent residual activity. The composition of the invention acts quickly and exhibits broad-spectrum bactericidal actions, which reduces the likelihood of resistance developing, and is thus suitable for treating or preventing chronic wounds.

The examples also show that the composition of the invention is able to treat pathogenic infections which contain a biofilm, and particularly biofilms which comprise VBNC cells, i.e. pathogenic infections that comprise pathogens in a VBNC state. In a preferred embodiment, the composition of the invention is for use in treating a bacterial infection comprising a Gram-positive and/or Gram-negative bacterial VBNC biofilm. In a particularly preferred embodiment, the composition of the invention is for use in treating a bacterial infection in/on a wound, where the wound comprises biofilm, and the biofilm comprises Gram-positive and/or Gram-negative bacteria, which may optionally be in a VBNC state.

The composition of the invention may also be used to treat a pathogenic infection in a wound as described herein whilst also healing the wound, which may happen simultaneously or sequentially. By "healing the wound" it is meant that the composition of the invention promotes the closure of the wound, i.e. it accelerates healing.

In a particular embodiment, the invention relates to a composition comprising:
benzalkonium chloride;
decyl dimethyl ammonium chloride;
poly hexamethylene biguanide hydrochloride;
bronopol;
p-chloro-m-cresol;
ethanol;
ethylene glycol; and
water,
for use in treating or preventing a bacterial and/or fungal infection of human or animal skin, where the composition is applied topically to the human or animal skin, or
for use in treating or preventing a bacterial and/or fungal infection in/on a wound, optionally where the composition additionally heals the wound, or
for use in treating or preventing a bacterial infection in/on a wound, where the wound is a chronic wound, and where the wound comprises a biofilm, optionally where the biofilm comprises VBNC cells.

In another embodiment, the invention relates to a composition comprising:
0.04-0.2 wt % benzalkonium chloride;
0.04-0.2 wt % decyl dimethyl ammonium chloride;
0.04-0.2 wt % poly hexamethylene biguanide hydrochloride;
0.01-0.06 wt % bronopol;
0.0005-0.005 wt % p-chloro-m-cresol;
0.05-0.3 wt % ethanol;
0.01-0.07 wt % ethylene glycol; and
the balance being water,
for use in treating or preventing a bacterial and/or fungal infection of human or animal skin,
where the composition is applied topically to the human or animal skin, or
for use in treating or preventing a bacterial and/or fungal infection in/on a wound, optionally where the composition additionally heals the wound, or
for use in treating or preventing a bacterial infection in/on a wound, where the wound is a chronic wound, and where the wound comprises a biofilm, optionally where the biofilm comprises VBNC cells.

In another embodiment, the invention relates to a composition comprising:
0.15 wt % benzalkonium chloride;
0.15 wt % decyl dimethyl ammonium chloride;
0.165 wt % poly hexamethylene biguanide hydrochloride;
0.045 wt % bronopol;
0.002 wt % p-chloro-m-cresol;
0.245 wt % ethanol;
0.05 wt % ethylene glycol; and
99.2 wt % water
for use in treating or preventing a bacterial and/or fungal infection of human or animal skin,
where the composition is applied topically to the human or animal skin, or
for use in treating or preventing a bacterial and/or fungal infection in/on a wound, optionally
where the composition additionally heals the wound, or
for use in treating or preventing a bacterial infection in/on a wound, where the wound is a chronic wound, and where the wound comprises a biofilm, optionally where the biofilm comprises VBNC cells.

In another embodiment, the invention relates to a composition comprising:

0.045 wt % benzalkonium chloride;

0.045 wt % decyl dimethyl ammonium chloride;

0.0495 wt % poly hexamethylene biguanide hydrochloride;

0.0135 wt % bronopol;

0.0006 wt % p-chloro-m-cresol;

0.0735 wt % ethanol;

0.015 wt % ethylene glycol; and 99.76 wt % water.

for use in treating or preventing a bacterial and/or fungal infection of human or animal skin, where the composition is applied topically to the human or animal skin, or for use in treating or preventing a bacterial and/or fungal infection in/on a wound, optionally where the composition additionally heals the wound, or for use in treating or preventing a bacterial infection in/on a wound, where the wound is a chronic wound, and where the wound comprises a biofilm, optionally where the biofilm comprises VBNC cells.

(ii) Treating or Preventing Rosacea, Eczema and/or Psoriasis

Any one of the compositions defined herein may be used to treat or prevent, most preferably treat, rosacea, eczema or psoriasis. Thus, the present invention also relates to a composition as defined herein for use in treating rosacea, eczema or psoriasis, preferably psoriasis and/or eczema. As is shown in the examples, the inventors have surprisingly found that the compositions of the invention also treat skin infections which are not, or are not caused by, pathogenic infections.

(iii) Healing Wounds

Any one of the compositions of the invention described herein may also be used to heal a wound, i.e. accelerate the closure of a wound. Thus, the compositions of the invention may be used to heal wounds (without necessarily treating a pathogenic infection in/on the wound).

However, treating a pathogenic infection in/on a wound contributes to the healing of a wound, i.e. the successful treatment of pathogenic infections in/on wounds using the compositions of the invention contributes to the healing of the wound. Thus, in a preferred embodiment, the composition of the invention is used to treat a pathogenic infection in/on a wound as described herein whilst also healing the wound, i.e. accelerating the healing/closure of the wound, which may happen simultaneously or sequentially. In a particularly preferred embodiment the composition of the invention is used to treat or prevent a bacterial and/or a fungal infection in/on the wound and heal the wound.

The wound may be any wound as described herein, for example a cut, burn, puncture or ulcer. In a preferred embodiment, the wound is a chronic wound. In a more preferred embodiment, the wound is a chronic wound comprising a biofilm. In another preferred embodiment, the composition of the invention used to heal the wound comprises at least 99.76 wt % water.

(iv) Killing or Inactivating a Virus on a Surface

Any one of the compositions of the invention described herein may be used to kill or inactivate a virus on a surface. Thus, the invention also relates to a method of killing or inactivating a virus on a surface, the method comprising applying a composition of the invention to the surface.

As is shown in Examples 8 and 9, the composition of the invention is able to kill or inactivate viruses on surfaces even at low concentrations, i.e. even when the composition comprises a large amount of water, e.g. more than 99% water by weight.

The surface may be any surface containing the virus. Non-limiting examples of surfaces include floors, table tops, veterinary operating theatres, hospital operating theatres and kitchen side boards, having any angle relative to ground level and of any shape, i.e. reference to surfaces is not limited to flat surfaces. The surface may be made from any material, e.g. plastic, wood, metal and the like. In a preferred embodiment, the surface is a plastic or metal, e.g. steel, surface.

In an embodiment, the method of killing or inactivating a virus is not a method for treatment on the human or animal body by therapy.

Viruses that may be killed or inactivated on a surface by the composition of the invention are coronavirus, for example human coronavirus 229E (HuCoV-229E), norovirus, for example murine norovirus 1 (MNV-1) strain CW1 and herpes. Preferred viruses that may be killed or inactivated on a surface by the composition of the invention are coronavirus 229E (HuCoV-229E) and murine norovirus 1 (MNV-1) strain CW1.

As is shown in Examples 8 and 9, the composition of the invention kills or inactivates even the most robust viruses, e.g. murine norovirus 1 (MNV-1) strain CW1, on surfaces.

In an embodiment the surface is pre-treated with the composition. By pre-treated it is meant that the composition is applied to the surface before a virus is identified on the surface, i.e. the composition of the invention is used a preventative measure against viruses on a surface.

When applied to a surface the composition of the invention prevents growth/activation of the virus on the surface for a long time period after application of the composition to the surface. In an embodiment, the composition kills or inactivates viruses on the surface for at least 1 hour after application of the composition on the surface. In a preferred embodiment, the composition kills or inactivates viruses on the surface for at least 24 hours after application of the composition on the surface. In another preferred embodiment, the composition kills or inactivates viruses on the surface for at least 48 hours after application of the composition on the surface.

Many modifications and variations of the embodiments described herein may be made without departing from the spirit and scope of the invention, as is apparent to those skilled in the art. The specific embodiments described herein are offered by way of example only.

EXAMPLES

The compositions of the invention used in the examples contained the following components.

Composition of the Invention (83.9 wt % Water):

3 wt % benzalkonium chloride;

3 wt % decyl dimethyl ammonium chloride;

3.3 wt % poly hexamethylene biguanide hydrochloride;

0.9 wt % bronopol;

0.04 wt % p-chloro-m-cresol;

4.9 wt % ethanol;

1.0 wt % ethylene glycol; and 83.9 wt % water.

Composition of the Invention (99.2 wt % Water):

0.15 wt % benzalkonium chloride;

0.15 wt % decyl dimethyl ammonium chloride;

0.165 wt % poly hexamethylene biguanide hydrochloride;

0.045 wt % bronopol;

0.02 wt % p-chloro-m-cresol;

0.245 wt % ethanol;

0.05 wt % ethylene glycol; and 99.2 wt % water.

Composition of the Invention (99.76 wt % Water);

0.045 wt % benzalkonium chloride;

0.045 wt % decyl dimethyl ammonium chloride;

0.0495 wt % poly hexamethylene biguanide hydrochloride;

0.0135 wt % bronopol;

0.0006 wt % p-chloro-m-cresol;

0.0735 wt % ethanol;

0.015 wt % ethylene glycol; and 99.76 wt % water.

All of the examples provided herein involved experiments which were performed under non-disclosure agreements.

Example 1—Treatment of Acute Widespread Impetigo

A 55y old female patient had acute widespread impetigo. Initially she was misdiagnosed as having athlete's foot fungal infection by a local pharmacist, which allowed the infection to proliferate and spread without control for 2 weeks. The pharmacist prescribed Clotrimazole/Canestin cream twice daily together with a thorough washing and drying procedure. The patient adhered strictly to this, some days dressing and cleaning four times a day. The condition continued to worsen with her feet swelling to the point where she was unable to fit into closed shoes. Furthermore, similar expressions of rash like infection began to appear on her arms, chest, neck and face, with accompanying low grade fever.

The patient then attended University College Hospital A&E where impetigo was immediately diagnosed. Due to the acute and extensive nature of the infection, oral antibiotics were advised and prescribed. The patient sought a non-oral alternative because of her history of anaphylactic reactions to primarily penicillin class antibiotics. The resident practitioner stated that the antibiotic cream would not be a problem with her allergy but perhaps insufficient to adequately treat her extensive infection. Clindamycin ointment was prescribed with advice that if symptoms were not improving within 48 hours to return to A&E for an oral Clindamycin.

The Clindamycin ointment initially seemed to help, with exudations seeming slightly abated. The sites of treatment appeared inflamed but infection seemed to be reducing so applications continued. Then, the areas of sites were increasing in redness/inflammation and swelling. Topical treatment was halted after first morning applications. Swelling continued through day and night, with constrictions to breathing and swallowing and chest pain—a typical anaphylactic response. National Health Service (NHS) direct was consulted, and an ambulance attended to the patient, but told the told they did not carry epinephrine pens.

The patient then attended local GP clinic appointment whereby epinephrine was promptly administered to stop further allergic reaction. Impetigo infection was however still present and continuing. It was on top of the patient's feet, ankles, forearm, chest, neck and face. Corticosteroids were prescribed by the GP, which helped to reduce some swelling but did not abate infection.

Wipes comprising the composition of the invention (99.2 wt % water) were received from the applicant under a non-disclosure agreement and immediately swabbed on all infected areas. The patient noticed immediate sensation of cooling/soothing, and the itching notably subsided. The raised weeping rash began to dry and reduce. The composition was applied to all areas several times per day after thorough cleansing and drying of affected areas.

Notable improvement was seen with previous exudations visibly drying and though swelling still present, redness and itching was exponentially reduced—there was no more uncontrolled spread of infection. After one week of applications, some redness and swelling still appeared but with significantly reduced exudations, and no itching.

Use of the composition of the invention was continued for 4 weeks in decreasing applications from 3-4 times per day, to 2 times per day, to 1 time per day. After 4 weeks, the patient was all clear of impetigo infection.

In summary, the composition of the invention halted and controlled the rampant impetigo bacterial infection within 1 week, and expedited full recovery within 3-4 weeks. The patient saw no improvement, however, with known medicines such as antibiotic and corticosteroid treatment, thus illustrating that the composition of the invention is superior compared with known medicines. Pictures of the patient's feet before, during and after treatment with the composition of the invention are provided in FIG. 1.

Example 2—Treatment of Gram-Positive and Gram-Negative VBNC Bacterial (Biofilm) Wounds and Healing of the Wounds Tests were undertaken in an approved clinical study in India under a non-disclosure agreement utilising a non-evasive fluorescence based multi-spectral imaging device to capture 'before and after' images of trauma wounds treated with the composition of the invention (99.2 wt % water). This process allowed the presence (or lack thereof) of certain Gram-positive and Gram-negative VBNC (biofilm) pathogens along with automated wound dimensions to be detected and classified clinically within two minutes of imaging, without the addition of any external reagents. The device uses multispectral imaging combined with advanced computational algorithm and a proprietary state-of-the-art ML engine for spatial mapping and detection of pathogens.

Figure 2A:
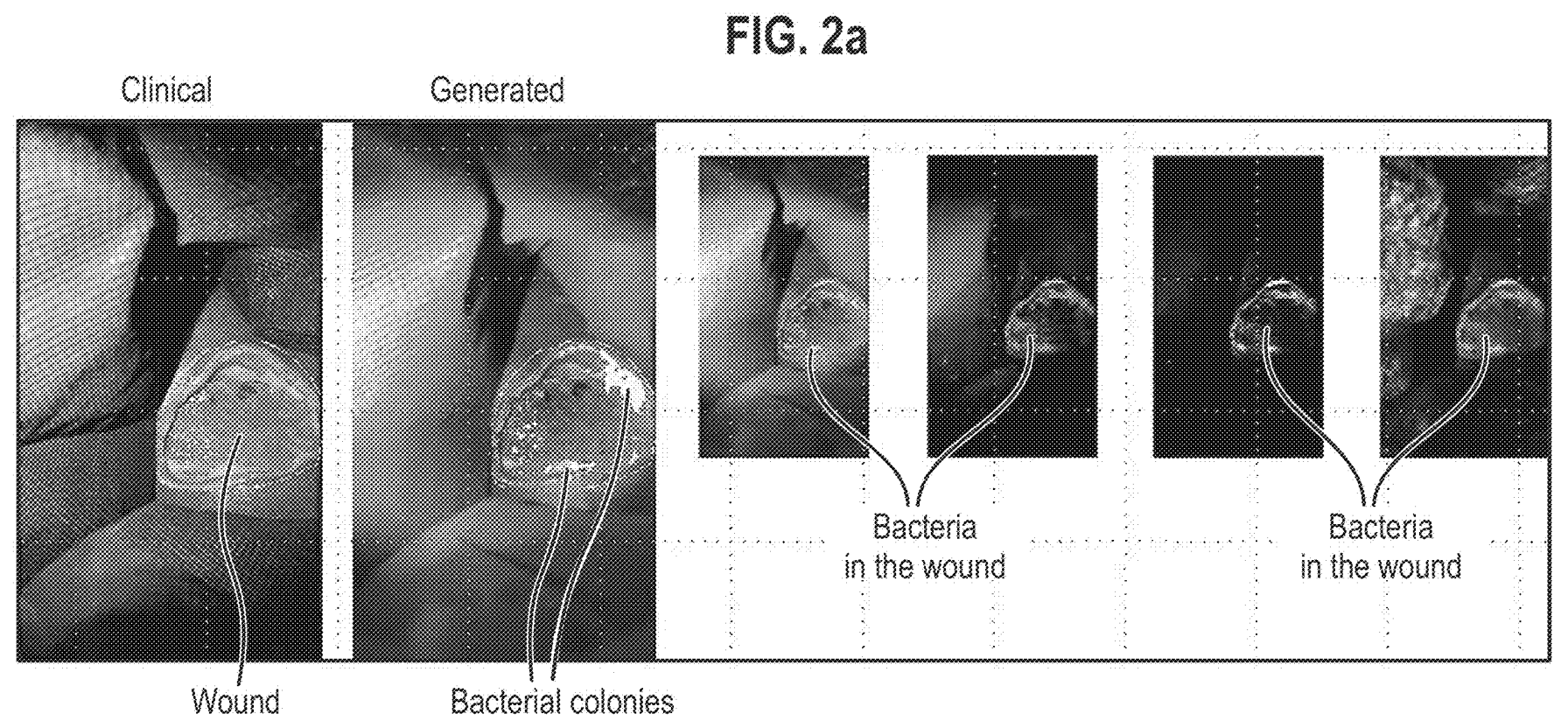
Figure 2B:
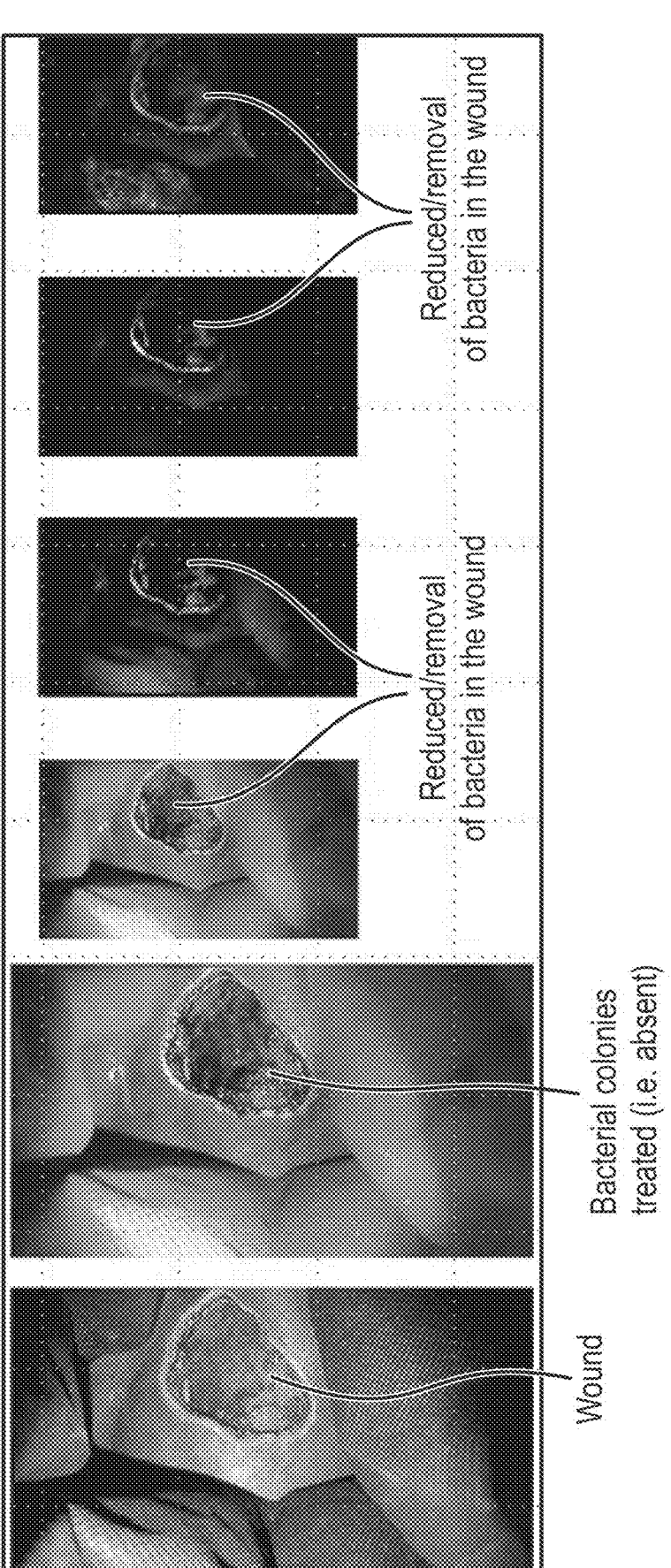

The results show that before the composition of the invention was applied to the wound (by way of a wipe) the wound contained a VBNC Gram-negative bacteria (in this case, *Klebsiella* sp.) in the form of a biofilm-FIG. 2*a*. Two minutes after the composition of the invention was applied, however, there was a complete absence of the bacteria and biofilm-FIG. 2*b*.

Similar results are shown in FIGS. 2*c-h*. In FIGS. 2*c-e*, a visible decrease in rod-shaped bacteria *Klebsiella* sp. and *P. aeruginosa* can be seen after application of the composition of the invention to a trauma wound, and in FIGS. 2*f-h* a visible decrease in *Klebsiella* sp. can be seen after application of the composition of the invention to a different trauma wound. The bacteria in these examples can be seen as initially present on muscle and connective tissue in/on the wound, and then to dramatically reduce after treatment with the composition of the invention.

In FIGS. 2*i-j*, MRSA, i.e. *S. aureus*, is shown to be reduced in a wound after application of the composition of the invention.

These surprising results have important implications because even if a wound were culturally 'clean', it may still be rendered non-healing because of the presence of the biofilm. However, the composition of the invention removed the biofilm (e.g. FIGS. 2*a-b*) completely and thus promoted improved healing without the use of systemic antibiotics.

Thus, because the compositions of the invention are able to remove Gram-positive and Gram-negative bacteria-containing biofilms in the VBNC state, the compositions of the invention can be utilised to promote treatment in chronic wounds (which are prone to biofilm formation), as well as trauma wounds, ulcers, burns, and the like. Given that biofilm-related infections lead to significant morbidity and mortality, the composition of the invention is thought to be of particular importance.

Example 3—Treatment of a Dog Bite and a Horse Leg Wound: Healing and Preventing a Pathogenic Infection An 82 year old man suffered a dog bite puncture (i.e. wound) to his finger. The composition of the invention (99.2 wt % water) was applied (under a non-disclosure agreement) immediately and daily and the wound healed rapidly and then completely in three weeks without infection. The male subject was adamant that using the composition of the invention contributed significantly to accelerating the healing process.

Figure 3B:
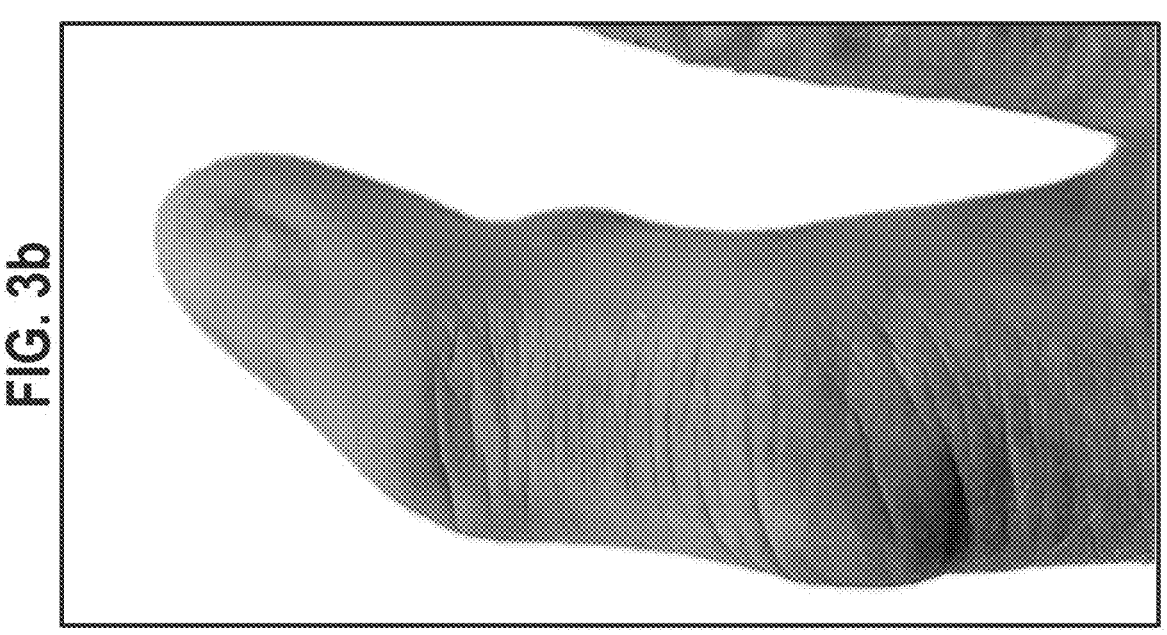
FIGS. 3a-b: Before and after images of a dog bite wound treated with a composition of the invention.
Figure 3A:

Before and after pictures of the wound and the healed wound are shown in FIGS. 3a and 3b (1 month later), respectively.

A 24 year old horse suffered a trauma wound that penetrated the tendon sheath on her front leg. Because of the high probability of infection based on past experience, the vet recommended the horse was immediately put to sleep on the basis that prognosis for recovery was very poor in a horse of that age. The owner refused and opted instead to suture and apply the composition of the invention (under a non-disclosure agreement) on a daily basis. To the vet's surprise, the horse suffered no obvious infection and made a full recovery.

Figures 4A, 4B:
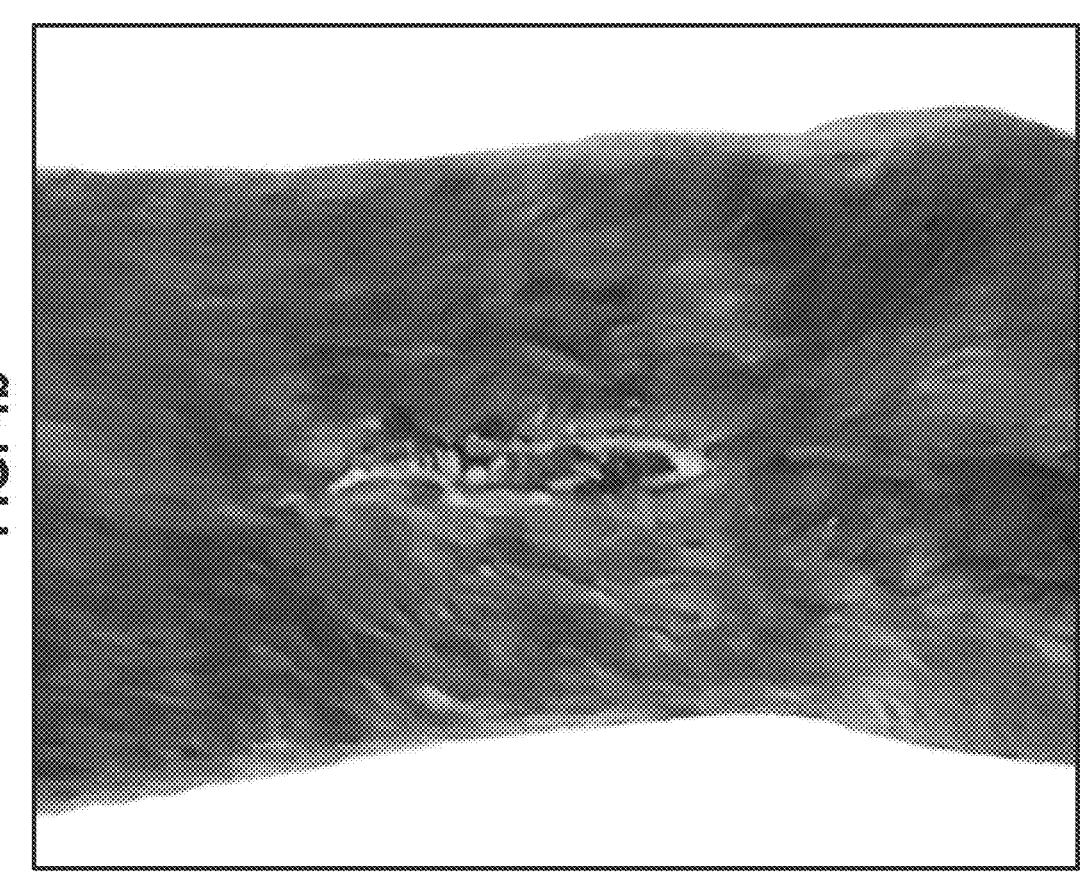
FIGS. 4a-b: Before and after images of a horse leg wound treated with a composition of the invention.

Before and after pictures (5 weeks apart) of the horse's leg are provided in FIGS. 4a and 4b, respectively.

Example 4—Treatment of a Fungal Nail Infection

A patient had tried various methods of treatment his fungal nail infection over the period of three years. After numerous visits to the doctor, nothing had worked.

The patient was introduced to the composition of the invention (99.2 wt % water) under a non-disclosure agreement and started to apply it to his nail. Just over a year later the nail cleared despite previous treatment methods not working. The patient rated the composition "10 out of 10" and also commented on the fact that it had no smell or greasy feel.

Figure 5A:
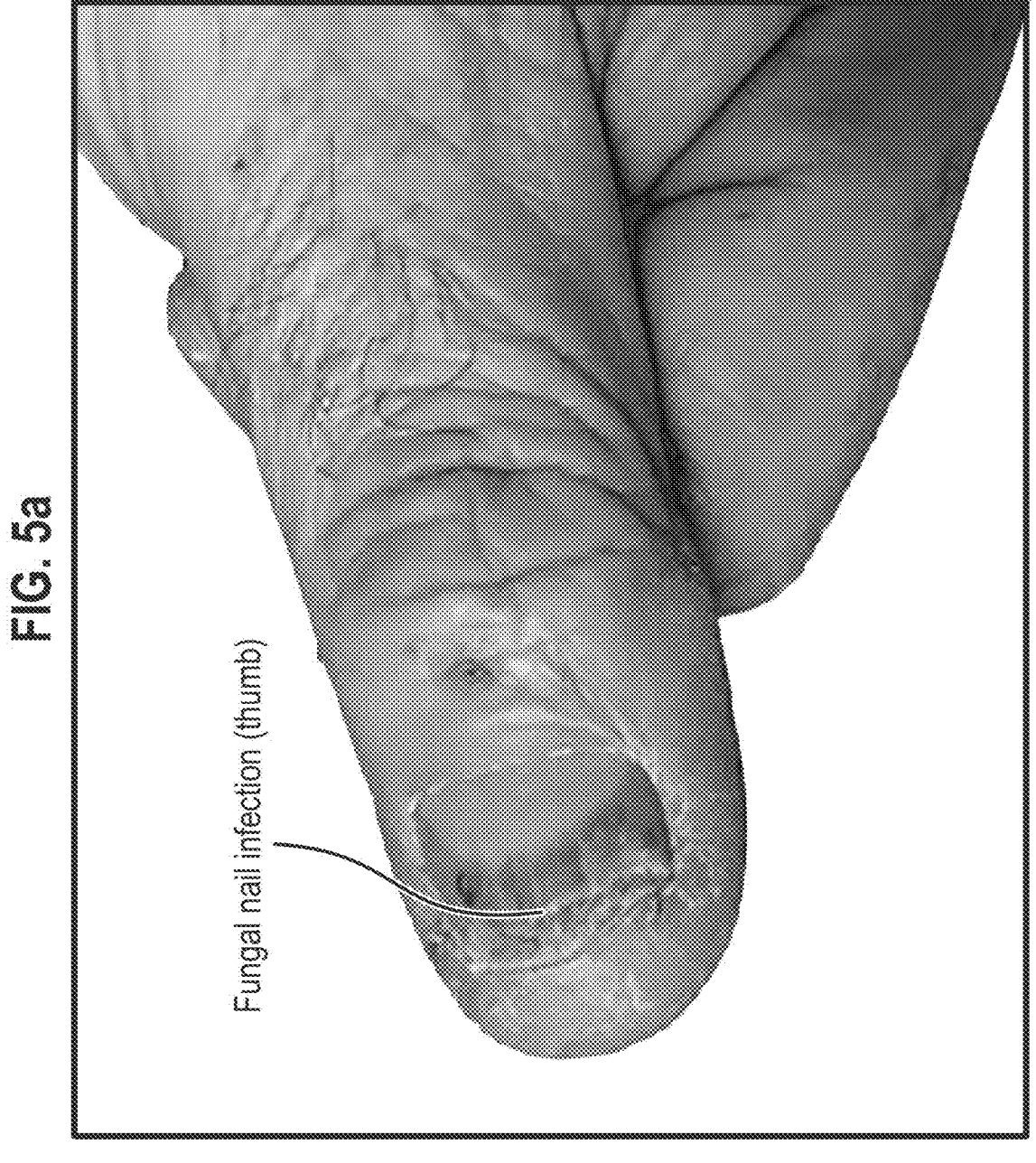
FIGS. 5a-c: Before and after images of treatment of a fungal nail infection with a composition of the invention.
Figures 5B, 5C:
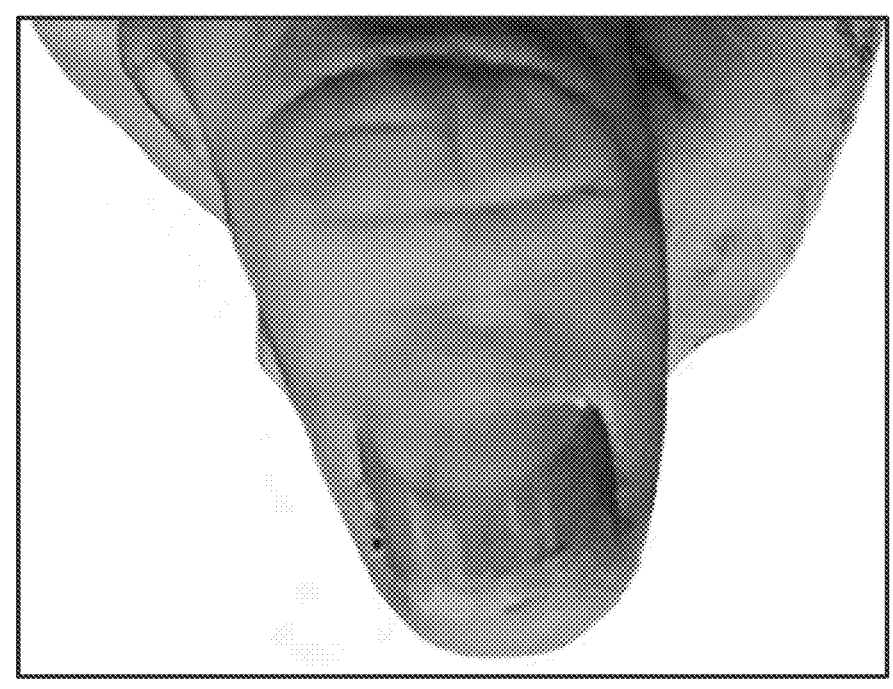

Pictures of the patient's thumb before during and after treatment with the composition of the invention are shown in FIGS. 5a, 5b, and 5c, respectively.

Example 5—Treatment of Psoriasis and Eczema on Human Skin within 48 Hours

The patient was 20 years old and had suffered from a long term skin condition diagnosed as psoriasis and eczema. She had used a range of OTC and RX medications with limited success. Following an attack, she opted to experiment with the composition of the invention (in this case, comprising 99.76 wt % water) under a non-disclosure agreement which she applied to the rash only on her hands and compared the results to the rash on her face. Initial application was at 0 hours and at 24 hours she reported that the skin on her hands reduced in irritation and became less sore with reduced redness. She again applied the composition of the invention at that time (24 hours) and observed thereafter at 48 hours that the symptoms on her hands had abated significantly and the rash was no longer moist or itchy and the skin colour had returned to almost normal. The area that were not treated, i.e. the patient's face, remained moist, sore, itchy and red.

Figure 10A:
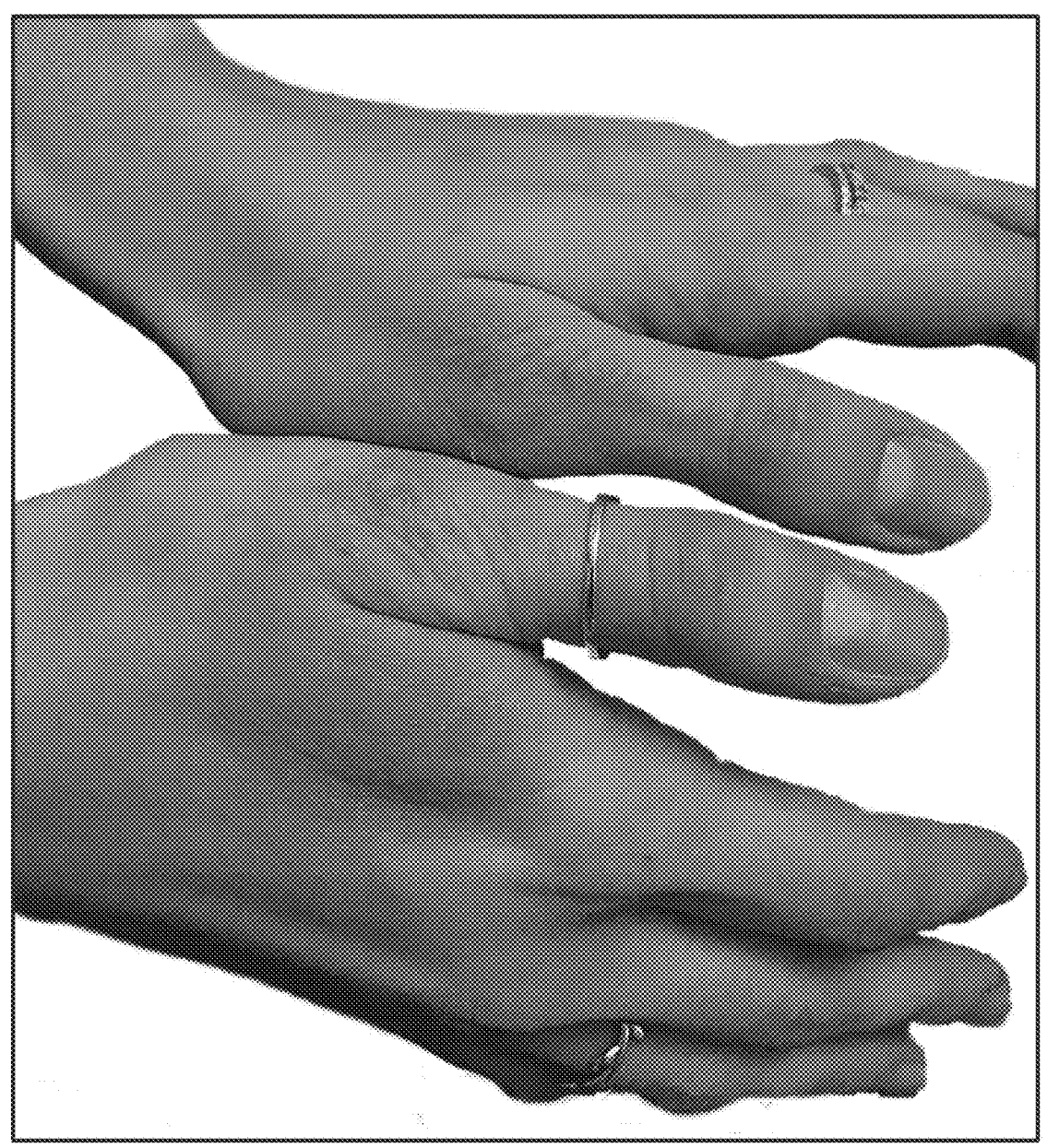
FIGS. 10a-b: Treatment of psoriasis and eczema on human skin using a composition of the invention.
Figure 10B:
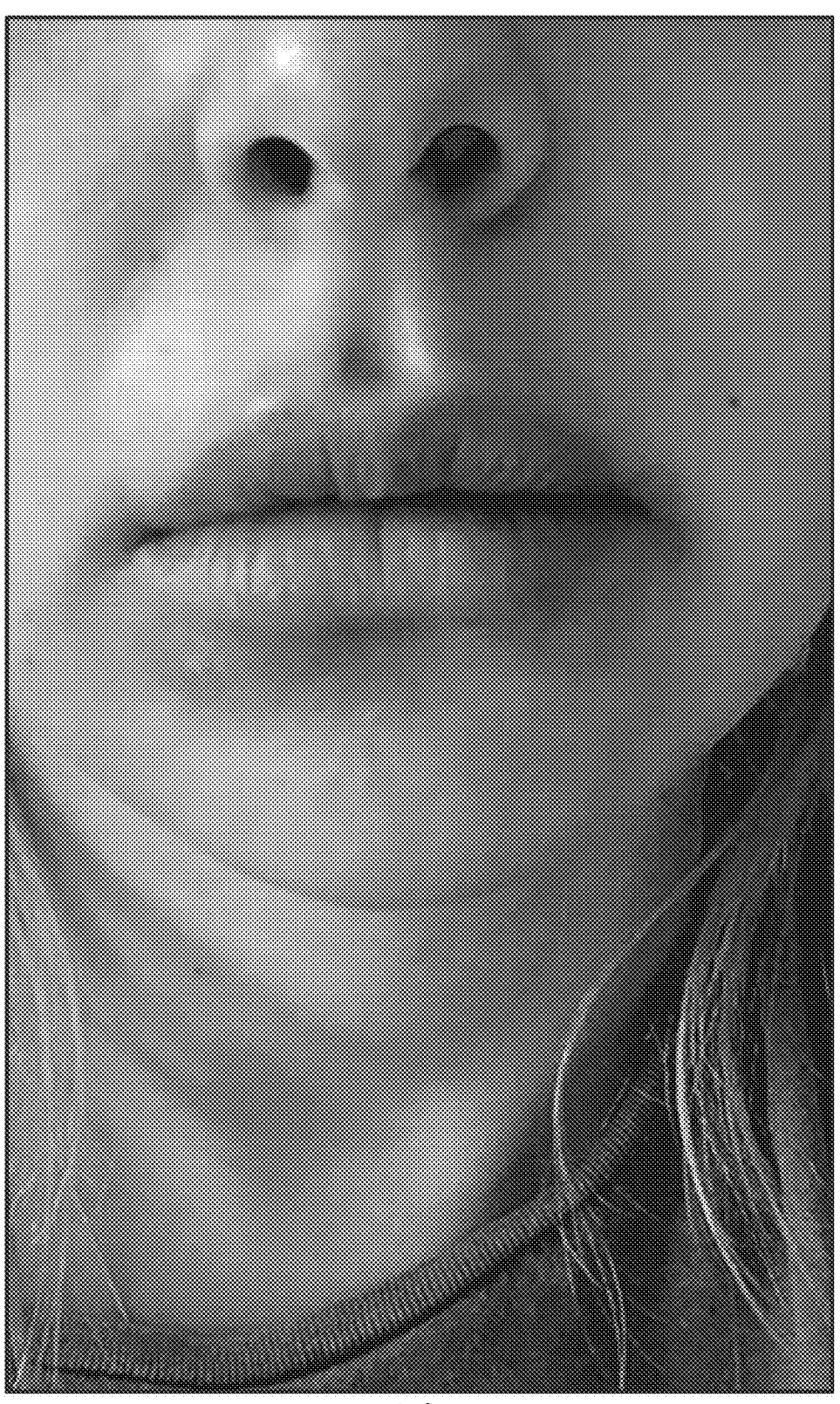

Before and after pictures of the patient's hands and face are shown in FIGS. 10a and 10b, respectively. These figures show that the untreated skin (i.e. the face) worsened over a 48 hour period, whereas the skin treated with the composition of the invention (i.e. the hands) showed dramatic improvement over the same time period.

Thus, not only does the composition of the invention treat pathogenic infections (e.g. of the skin) but it also treats skin conditions which are not caused by a pathogenic infection (e.g. psoriasis and/or eczema).

Example 6—Skin Irritation Tests

An in vitro evaluation of the irritancy potential of the composition of the invention using a tissue engineered human skin model was carried out by Dr David Voegeli, Associate professor of Nursing, at the Skin Health Research Group, under a non-disclosure agreement.

The overall aim of the project was to investigate the effects of several compositions of the invention on an approved tissue engineered human skin model (The European Union Reference Laboratory for alternatives to animal testing, EURL-ECVAM).

The objectives of the tests were as follows:
1. To determine the degree of skin irritancy caused by a range of compositions of the invention.
2. To determine in vitro toxicity of a range of compositions of the invention to human keratinocytes.

Results

Macroscopic and Microscopic Examination of Inserts

All tissues received were intact and viable on visual inspection and were used. Following dosing of the tissues a random selection of inserts were examined by low powered light microscopy to ensure no damage had been caused during the procedure. No cell damage was observed in any of the inserts examined.

MTT Assay

The raw optical density of each well at 570 nm obtained in the MTT assay is shown in FIG. 11:

Relative Viability

Figure 6:
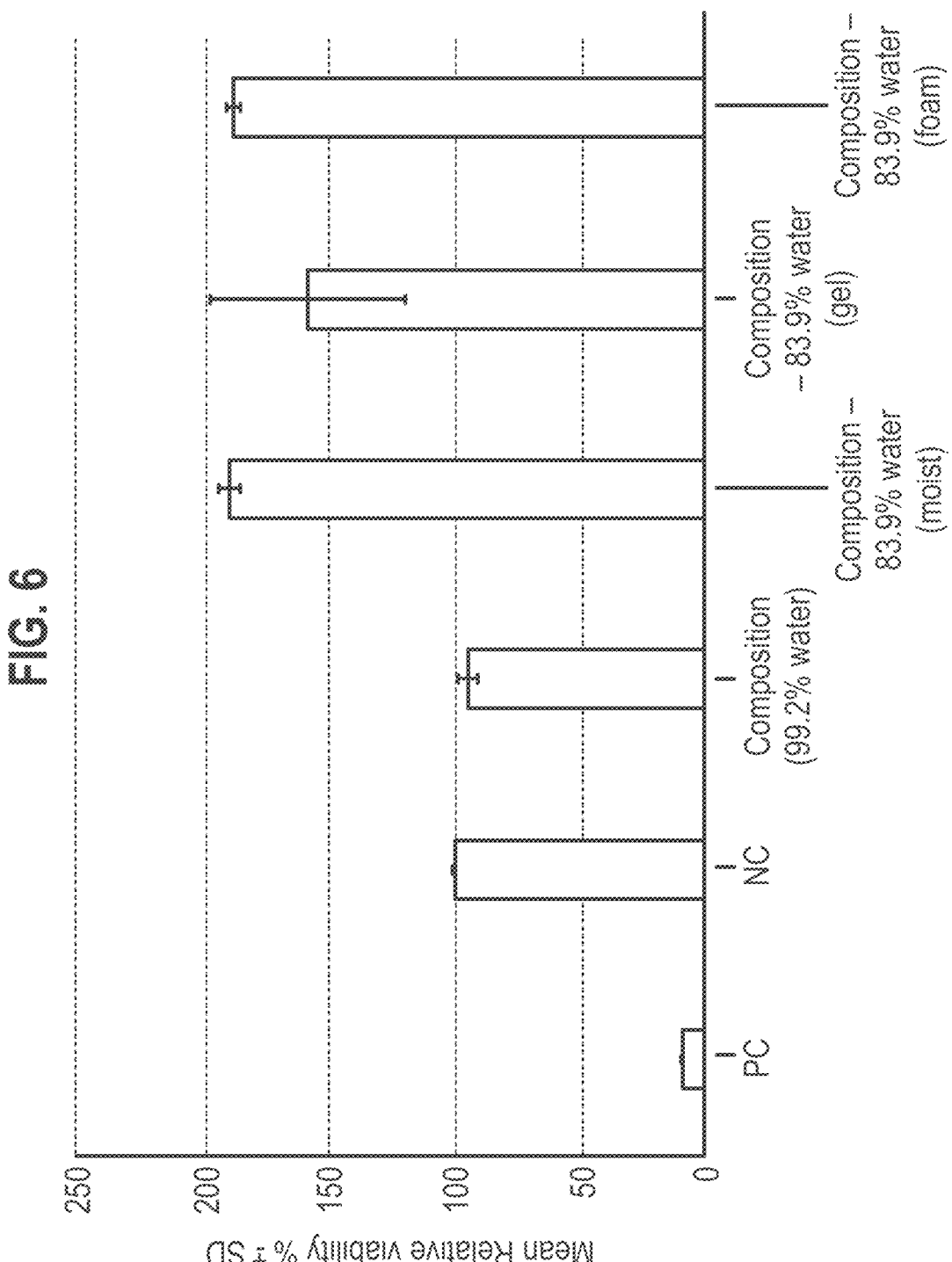
FIG. 6: Skin irritation test results for a composition of the invention

Calculation of the relative viability for the controls and compositions tested is shown below (Table 2) and summarised in FIG. 6:

TABLE 2

| Relative viability | |
| --- | --- |
| Formulation | Mean RV % |
| Positive control | 9.0 |
| Negative control | 100 |
| Composition of invention (99.2 wt % $H_2O$) | 94.9 |
| Composition of invention (83.9 wt % $H_2O$), Moist | 189.7 |
| Composition of invention (83.9 wt % $H_2O$), Gel | 158.4 |
| Composition of invention (83.9 wt % $H_2O$), Foam | 188.2 |

Conclusion

This study was designed to investigate the potential skin irritant effects of a range of compositions of the invention intended for topical application in humans/animals. A total of four products were tested, plus positive control and negative control. Calculation of RV % as a measure of irritancy showed all compositions of the invention tested had an RV % over 50, with the majority (75%) having an RV % above 100.

These data demonstrate that, unlike many known antiseptics in the art, none of the compositions tested would be likely to cause skin irritation, even for more concentrated compositions, e.g. compositions according to the invention comprising 16% water by weight.

Example 7—Non-Cytotoxicity

A composition of the invention was tested for cytotoxicity (according to ISO 10993-5) under a non-disclosure agreement. While it is not essential that the compositions of the invention are non-cytotoxic according to this test, it is an advantageous property.

A composition according to the invention (comprising 99.2% of culture medium) was found to be cytotoxic, i.e. complete cell death. However, a composition of the invention comprising 99.76% of culture medium was found to be non-cytotoxic (26% cell density decrease versus negative control—ISO 10993-5 accepts a cell growth inhibition of 30%).

Thus, the composition of the invention is non-cytotoxic when it comprises at least about 99.5% water by weight (e.g. at least 99.76% water by weight). As has been shown in Example 5 and Example 11, at this non-cytotoxic concentration the composition of the invention is surprisingly able to treat skin conditions such as psoriasis and eczema, and also has bactericidal activity against a range of bacteria in dirty conditions (i.e. in vitro conditions mimicking the conditions in/on a human/animal wound), and thus is able to treat pathogenic infections such as pathogenic infections in/on wounds and the infections illustrated in, for example, Examples 1-4.

Example 8—Killing and Inactivation of Coronavirus on Surfaces

Protocol

Two methods were performed under non-disclosure agreements, each at 21° C.:

i) A stainless steel (S30400) surface was pre-coated with the composition of the invention (in this case, containing 99.2 wt % water) and then challenged with virus; and ii) the virus was dried onto the stainless steel surface and then challenged with the composition of the invention (in this case, containing 99.2 wt % water).

The virus was then recovered from all surfaces and tested to see how much infectious virus (i.e. able to cause disease) remained after the treatment.

Preparation of a Range of Reagents

HuCoV-229E virus stock solution (a crude infected cell lysate): this virus was originally isolated from the upper respiratory tract of a man with bronchitis in 1960s. It has been used as a surrogate for the highly pathogenic coronaviruses that cause SARS and MERS which require specialised higher level containment facilities. HuCoV-229E is a Hazard Group 2 (HG2) virus that causes respiratory infection in humans unlike other surrogates, such as TGEV, which affects intestinal mucosa. In the majority of individuals infection with HuCoV-229E occurs every few years as the immune response fails to eradicate the virus over time. The virus preparation contains dead human lung cells and a complex mixture of biomolecules (including growth medium constituents) to simulate virus contamination in sputum and natural respiratory secretions.

Host cell line, MRC-5, normal human lung fibroblast cells (HuCov-229E can attach and replicate in this cell line).

Stainless steel coupons (1 cm$^2$×0.5 mm) was used as an example of a common surface material throughout.

Phosphate buffered saline (PBS), cell culture growth medium and supplements, trypsin/EDTA, low melting point agarose solution for overlay, neutral red stain.

Consumables

Disposable tubes (6 mL, 30 mL and 50 mL), glass beads, tissue culture flasks and 6 well trays, loops and spreaders, petri dishes, culture boxes, pipettes, tips, pastettes, syringe and syringe filters.

Equipment

Microbiological Safety Cabinet

Microbiological incubator (37° C., carbon dioxide is pumped into the incubator and maintained at 5% for optimal growth of the cells)

Micro centrifuge

Inverted microscope

Light box and magnifying lens

Test Procedures

The efficacy of the composition of the invention to inactivate HuCoV-229E was determined by 2 methods:

1. Pre-coat a non-biocidal surface with the composition of the invention for 1, 24 and 48 hours and investigate if virus is inactivated on contact i.e. if a surface has been cleaned with the composition of the invention will the residual layer inactivate any subsequent virus contamination of that surface in e.g. respiratory secretions in coughs and sneezes 2. Pre-coat a non-biocidal surface with virus and investigate if the composition of the invention applied for 0, 30 seconds, 5 or 10 minutes will inactivate the virus i.e. will cleaning an already contaminated surface with the composition of the invention inactivate the virus Experimental Protocol Pre-Experiment and Preparation:

Passage of cell line MRC-5 to sufficient quantities for the experiment. This involves passaging (cells adhere to plastic and have to be removed with trypsin/EDTA) every 3 days each time increasing the number of flasks. On the day before experiment cells are removed from approximately 10 tissue culture flasks (base 75 cm$^2$) re-suspended in fresh culture medium and seeded into 6 well trays where they will settle, attach and form a monolayer of cells on the base of each well.

Coat coupons with the composition of the invention for 24 and 48 hours prior to the experiment Day of the Experiment:

Check cells appear healthy and sub confluent before starting the experiment.

Inoculate stainless steel coupons (in triplicate) with either:

(1) the composition of the invention for 1 hour (20 μL the composition of the invention (99.2 wt % water) spread over the surface of coupon)—Method 1

(2) coronavirus for 1 hour (20 μL HuCoV-229E, approximately 103 plaque forming units, spread over the surface of the coupon (1 cm$^2$))—Method 2

To coupons for Method 1 add virus for 0, 30 seconds, 5 and 10 minutes or method 2 add the composition of the invention for same times Remove the virus the same way for each method by placing each coupon into separate tube of 5 mL growth medium (5% foetal calf serum)/glass beads (2 mm)

Vortex each for 15 s

Prepare 10 fold dilutions of each sample in growth medium

Remove medium from MRC-5 cells in each well of 6 well trays and add 1 mL test dilution and incubate 90 minutes at 37° C., 5% $CO_2$ (virus attaches to cells in this time)

Carefully remove the virus and add overlay. Refrigerate for 15 minutes to ensure overlay 'sets' and transfer to incubator.

Incubate 6 days at 37° C., 5% $CO_2$

Observation and Calculation of Infectious Virus that has been Recovered from Each Coupon:

Add 3 mL of a sterile filtered 3% solution of neutral red vital stain to each well Incubate 2 hours, remove liquid stain on top of the well and incubate a further hour. This stain is taken up by live cells and stains them red. Dead cells will not take up this stain. Where the virus has replicated inside the cells a plaque will be visible as an unstained area. This is really a hole in the cell monolayer where the infected cells have burst and died (lysed) surrounded by remains of dead infected cells. The overlay prevents virus spreading beyond the attachment time so plaques are distinct and easy to count.

Count plaques* and calculate the quantity of infectious virus recovered from each coupon. Take photographs as necessary. With regard to counting plaques, viral numbers are often expressed as plaque forming units (pfu) (not all viruses produce plaques), which is an approximate estimate of the amount of infectious virus present because it is difficult to express results as actual number of viruses.

Analyse the data using graphical software

Results

Figure 7E:
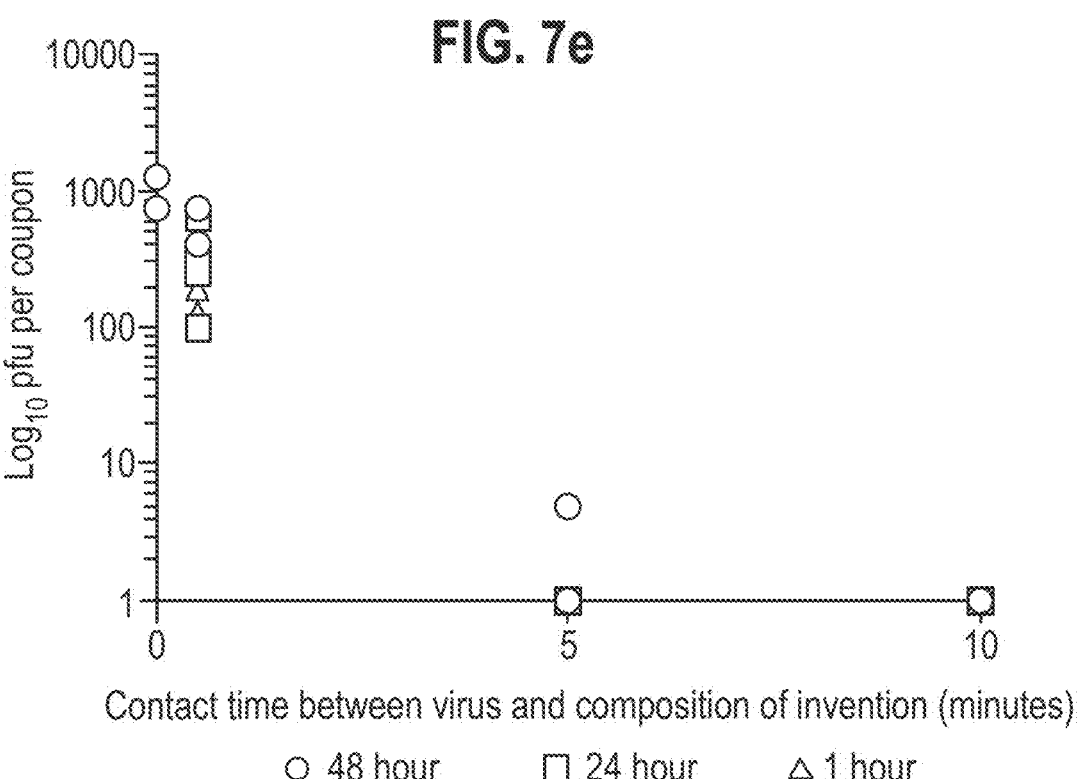

The Results are Shown in FIG. 7, and are Summarised Below:

The tables in FIGS. 7*a* and 7*b* contain raw data (average pfu recovered per surface coupon) and Log 10 reduction in infectious human coronavirus 229E (HuCoV-229E) for each contact time. Starting inoculum i.e. maximum amount of infectious virus per $cm^2$ with no treatment is 2500 plaque forming units (pfu).

FIGS. 7*a* and 7*c*-7*e* (method (1)): surface pre-coated with 10 µL composition of the invention per $cm^2$ for 48, 24 or 1 hour before application of virus.

Figure 7F:
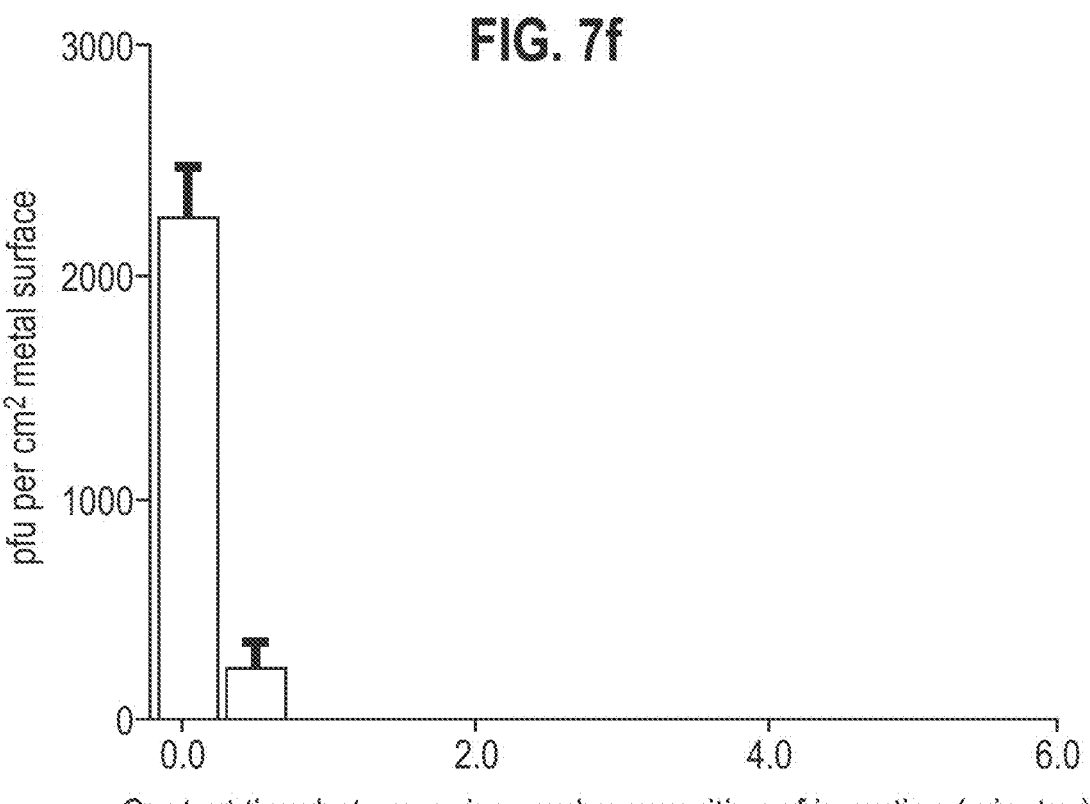
Figures 7G, 7H:
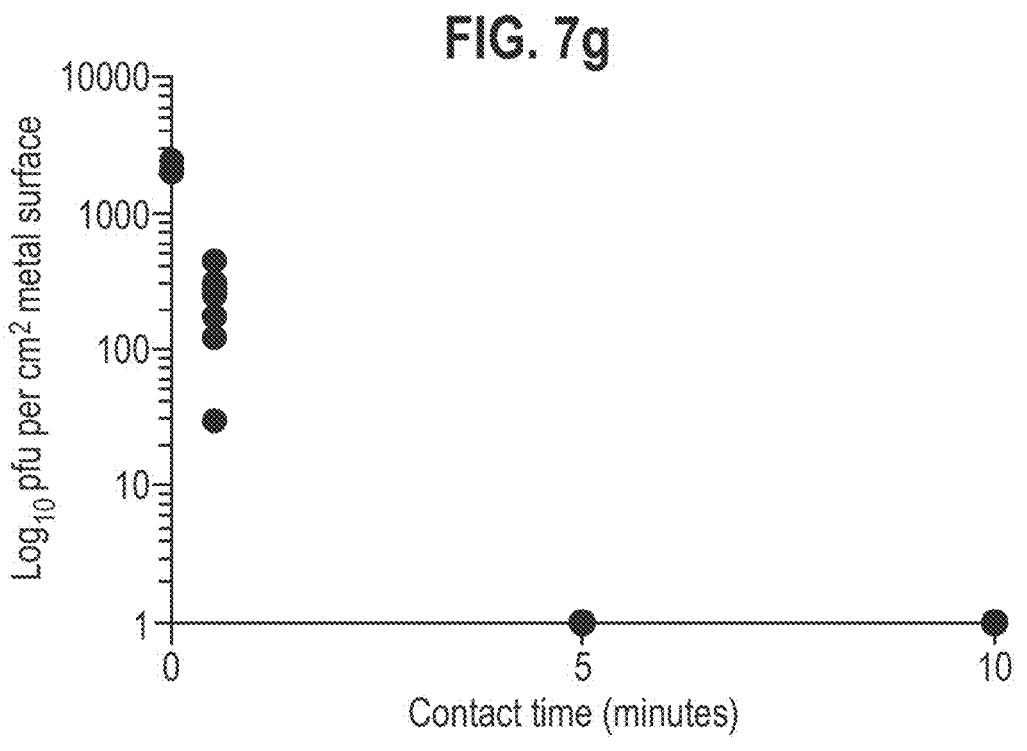

FIGS. 7*b* and 7*f*-7*g* (method (2)): surface pre-coated with 20 µL HuCoV-229E (2500 pfu) for 1 hour before application of composition of the invention.

FIG. 7*h*=rate of inactivation in 30 seconds for methods (1) and (2).

Log reduction in infectious virus was calculated according to the following formula:

Log reduction=log 10 (pfu before treatment) minus log 10 (pfu after treatment)

1-log reduction=90% reduction 2-log reduction=99% reduction 3-log reduction=99.9% reduction 4-log reduction=99.99% reduction 5-log reduction=99.999% reduction 6-log reduction=99.9999% reduction The results, in summary, show that the composition of the invention is very effective against human coronavirus 229E, even when used at very low concentrations.

In addition, the results show that coating the surface with the composition of the invention continued to inactivate the virus for long periods—there was no difference between coating for 1 hour and 24 hours and only a slight reduction in efficacy was observed with surfaces coated for 48 hours. All viruses were inactivated within 30 seconds to 5 minutes.

The composition of the invention was very effective against dried virus and also inactivated it within 30 seconds to 5 minutes.

The composition of the invention is therefore able to continually inactivating any surface for long periods of time, which is useful, for example, for contamination that occurs between cleaning regimes.

Example 9-Killing and Inactivation of Norovirus on Surfaces

The purpose of these experiments was to determine whether compositions of the invention (in this case, comprising 99.2 wt % water) could kill or inactivate murine norovirus. Three experiments were conducted under non-disclosure agreements, as summarised below.

Experimental Protocols

Viral Strains and Cell Lines

Murine norovirus 1 (MNV-1) strain CW1, and the mouse monocyte macrophage line RAW 264.7 were supplied by Professor Herbert Virgin IV, Washington University, US. The semi-adherent cell line was maintained at sub-confluence to prevent loss of characteristic phenotype and maintained in HEPES buffered Dulbecco's Modified Eagle Medium (DMEM) containing GlutaMAX, 25 mM D-glucose, 10% foetal bovine serum and without sodium pyruvate at 37° C. in the presence of 5% $CO_2$. The cells adhere to tissue culture grade plastic through cation-dependent and independent receptors but can easily be removed by scraping.

Preparation of Sample Surfaces

Stainless steel coupons (10×10×0.5 mm) were degreased in acetone, stored in absolute ethanol and flamed prior to use.

Inoculation of Metal Coupons with MNV-1 (to Simulate Wet Fomite Contamination) and Assessment of Infectious Virus by the Detection of Cytopathic Effect in Murine Cell Line (Plaque Assay)

The surfaces of coupons were inoculated with MNV-1 1.2×105 plaque forming units (pfu) in 20 µL (6×106 PFU/ml) to represent wet fomite (dries in 30-40 minutes at 22° C.). Drying time was included in the exposure time. Viruses were removed from the coupons at 2 hours by vortexing for 30 seconds in 2 ml complete DMEM with approximately 50×2 mm diameter glass beads. A range of dilutions was prepared immediately in complete DMEM and 1 mL aliquots were plated onto monolayers of RAW 264.7 that had been seeded with 106 cells per well of 6 well plates (diameter 3.5 cm) 3 hours previously, and incubated at 37° C. and 5% $CO_2$ for 90 minutes. The inoculum was aspirated and overlay of 3 mL per well of 3% low melting point (LMP) agarose in complete medium was added to prevent virus spreading to other cells. Plates were incubated for 15 minutes at 4° C. until set and then at 37° C., 5% $CO_2$ for 72 hours. Monolayers were stained with 2 mL per well of a filtered 0.01% solution of the supravital stain, Neutral Red, which is pinocytosed by viable cells and accumulates in the cell lysosomes staining the cells red, in PBS for 2 hours at 37° C. and 5% $CO_2$. Excess stain was removed and the plates re-incubated for a further hour. Plates were stored overnight at 4° C. to increase definition of plaques which were counted and used to calculate pfu recovered per coupon.

Modifications to Above Protocol

1. Virus Added to Coupons Pre-Coated in a Composition of the Invention

Twenty hours prior to experiment, steel coupons were coated with 20 μl of the composition of the invention or sterile, distilled water. The liquid was spread over the whole surface, and allowed to dry. Coupons were then stored at room temperature until required for the assay, and virus was added on top of this pre-coated layer. The assay continued as detailed above.

2. Composition of the Invention Added to Coupons Pre-Coated in Virus

Forty minutes before the assay started, the surfaces of coupons were inoculated with MNV-1 1.2×105 plaque forming units (pfu) in 20 μL. Once dry, the surfaces were subsequently coated with the composition of the invention or sterile, distilled water. After two hours incubation, the assay continued as above.

3. Coupons Pre-Coated in the Composition of the Invention, then Virus is Applied, and then More Composition of the Invention Two hours prior to the assay start, steel coupons were coated with 20 μl of the composition of the invention or sterile, distilled water. Forty minutes before the assay started, the surfaces of coupons were inoculated with MNV-1 1.2×105 plaque forming units (pfu) in 20 μL. Once dry, the surfaces were subsequently coated with the composition of the invention or sterile, distilled water. After two hours incubation, the assay continued as above. Coupons only received one type of treatment, resulting in two doses of the composition of the invention or distilled water.

Experiments and Results.

The effect of the composition of the invention pre-coated onto surfaces on murine norovirus A 20 μl aliquot of the composition of the invention was applied to stainless steel surfaces. This was allowed to dry overnight at room temperature to mimic regular routine cleaning of surfaces. A virus suspension was then applied to the pre-coated surface, to mimic droplets that are spread by human transmission during a norovirus outbreak. After 2 hours incubation on the steel surface pre-coated with the composition of the invention, the virus infectivity was decreased by 1- and 2-log respectively (Table 3 and FIG. 8a). As the composition of the invention had been applied to the steel surface 20 hours before, this indicates that it remains active whilst dried onto surfaces for some time.

TABLE 3

| | Viral PFU/201 after various treatments with the composition of the inventor | | |
| --- | --- | --- | --- |
| Treatment | Average PFU/20 μl | Log reduction | % kill |
| Control = virus only | 1.22E+05 | 1.00E+00 | 0 |
| Virus + composition of invention (99.2 wt % H₂O) | 1.73E+02 | 4.28E+02 | 99.77 |
| Composition of invention (99.2 wt % H₂O) pre-coated steel + virus | 5.97E+03 | 4.04E+01 | 97.52 |
| Composition of invention (99.2 wt % H₂O) pre-coated steel + virus + application of composition of invention (99.2 wt % H₂O) | <2.00E+01 | >2.52E+03 | >99.96 |

The effect of the composition of the invention applied directly onto murine norovirus A 20 μl aliquot of virus suspension was dried onto a steel surface to mimic virus-containing water droplets spread by human transmission. This was then treated with 20 μl the composition of the invention to mimic surface cleaning procedures after an outbreak. After 2 hours incubation, the virus infectivity was decreased by 2-log (Table 3 and FIG. 8b).

The effect of the composition of the invention on dried surfaces and applied directly onto murine norovirus Stainless steel surfaces were pre-coated with the composition of the invention, a viral suspension was applied to the surface, and then the composition of the invention was re-applied to the surface and allowed to incubate for 2 hours. This study was to mimic routine cleaning procedures, a norovirus outbreak, and then a second round of surface decontamination. After two hours incubation at room temperature with these applications of the composition of the invention, it was observed that the virus infectivity had been decreased by at least 3-log for the composition of the invention (Table 3 and FIG. 8b).

Summary of Results

The composition of the invention (comprising 99.2 wt % water) was able to kill or inactivate Murine norovirus (MNV-1) by 2-log by directly treating contaminated surfaces. If surfaces were pre-treated with the composition of the invention, the viral load of the surface could be reduced by 1-log due to the long-lasting effects of the composition on the surface, and if the surface was treated both before and after the viral contamination event, a greater than 3-log reduction of virus could be seen (FIG. 8c).

Example 10: MICs for a Range of Gram-Positive and Gram-Negative Bacteria for the Composition of the Invention The composition of the invention has a broad spectrum of activity, at low concentrations, encompassing a wide range of Gram-positive and Gram-negative bacteria, as shown in FIG. 9. FIG. 9 shows the MIC of the composition of the invention against a range of bacteria in a standard bacteriological culture environment.

Thus, this example illustrates that the composition of the invention has a broad spectrum of activity covering Gram-positive, Gram-negative and spore-forming bacteria, which is a requirement in the treatment of, for example, chronic wounds. This example, in combination with Examples 1-7 and 11, illustrates that the composition of the invention has a broad spectrum of activity against bacteria in the treatment of pathogenic infections in a human or animal, such as a pathogenic infections in/on a wound.

Example 11—Bactericidal Activity of the Composition of the Invention Under Dirty Conditions Tests were carried out by Abbott Analytical Ltd. under a non-disclosure agreement to evaluate the activity of the composition of the invention against a range of bacteria under dirty conditions (defined below).

Test Method and its Validation

Method=Dilution-neutralisation

Neutraliser=30.0 g/l Polysorbate 80+3.0 g/l Lecithin+1.0 g/l L-histidine+1.0 g/l L-cysteine (Neutraliser A)

Neutraliser validation=Validated in accordance with EN 13727:2012+A2:2015 (5.5.2)

Experimental Conditions

Contact time=5 minutes±10 seconds

Test temperature=20±1° C.

Interfering substance=3.0 g/l bovine albumin+3.0 ml/l sheep erythrocytes ("dirty conditions")

Temperature of incubation

Requirements

Bactericidal activity was defined as at least 5.00 log (lg) reduction.

Results

| Bacterial strain | Concentration of composition of the invention (wt % $H_2O$) | 1 g reduction |
| --- | --- | --- |
| *Pseudomonas aeruginosa* | 99.2 and 99.76 | >5.51 and >5.32 |
| *Acinetobacter baumannii* | 99.2 | >5.45 |
| *Corynebacterium amycolatum* | 99.2 and 99.76 | >5.03 and >5.03 |
| *Corynebacterium striatum* | 99.2 and 99.76 | >5.51 and >5.36 |
| *Escherichia coli* K12 | 99.2 | >5.33 |
| *Staphylococcus aureus* | 99.2 | >5.47 |
| *Eneterococcus hirae* | 99.2 | >5.09 |

Conclusions

The composition of the invention shows bactericidal activity according to EN 13727:2012+A2:2015 against a range of bacteria under dirty conditions. The dirty conditions (which are defined above) were chosen because they correspond to the conditions found in/on human/animal wounds. The range of bacteria tested in this study include the bacteria which are most commonly found in wounds, particularly chronic wounds. For example, several studies have highlighted that the majority of chronic wounds contain *S. aureus*, with just over half also containing *P. aeruginosa*.

Both of these bacteria, and other bacteria commonly found in wounds, were tested in this study.

The results show that the composition of the invention has >51 g reduction against the bacteria which are most commonly found in wounds when tested in an environment which mimics a real-life wound environment. Furthermore, the composition of the invention was shown to be active against these bacteria even at very low concentrations, i.e. even when the composition contains at least 99.2 wt % water (e.g. 99.76 wt % water).

Thus, the composition of the invention has surprisingly been found to be capable of treating a range of bacterial infections in/on wounds, even when used at very low concentrations.

The invention claimed is:

1. A method of healing a wound in a human or animal subject, the method comprising administering a composition to the wound of the subject, the composition comprising:

0.04-0.2 wt % benzalkonium halide;

0.04-0.2 wt % decyl dimethyl ammonium halide;

0.04-0.2 wt % poly hexamethylene biguanide salt;

0.01-0.06 wt % bronopol; and 0.0005-0.005 wt % p-chloro-m-cresol.

2. The method of claim 1, wherein the wound comprises a pathogenic infection, preferably wherein the wound comprises a bacterial infection and/or a fungal infection.

3. The method of claim 2, wherein the wound comprises a bacterial infection.

4. The method of claim 1, wherein the wound is a chronic wound.

5. The method of claim 1, wherein the wound is a cut, burn, puncture or ulcer.

6. The method of claim 1, wherein the composition additionally comprises at least 99.76% water by weight.

* * * * *